US008277455B2

(12) United States Patent  (10) Patent No.: US 8,277,455 B2
Couture et al.  (45) Date of Patent: Oct. 2, 2012

(54) UNIVERSAL POSITIONING DEVICE FOR ORTHOPEDIC SURGERY AND METHOD OF USE THEREOF

(75) Inventors: Pierre Couture, Montreal (CA); Louis-Philippe Amiot, Hampstead (CA)

(73) Assignee: Orthosoft Inc., Montreal (CA)

( * ) Notice: Subject to any disclaimer, the term of this patent is extended or adjusted under 35 U.S.C. 154(b) by 411 days.

(21) Appl. No.: 12/626,645

(22) Filed: Nov. 26, 2009

(65) Prior Publication Data

US 2010/0121334 A1  May 13, 2010

Related U.S. Application Data

(63) Continuation of application No. PCT/CA2008/001272, filed on Jul. 9, 2008.

(60) Provisional application No. 60/948,546, filed on Jul. 9, 2007.

(51) Int. Cl.
  *A61B 17/58*  (2006.01)
  *A61B 17/60*  (2006.01)
  *A61F 2/00*  (2006.01)

(52) U.S. Cl. ........................................................ 606/88

(58) Field of Classification Search ............... 606/87–89
See application file for complete search history.

(56) References Cited

U.S. PATENT DOCUMENTS 4,703,751 A * 11/1987 Pohl .................................. 606/62
7,377,924 B2 * 5/2008 Raistrick et al. ................. 606/87
2005/0171545 A1   8/2005 Walsh et al.

OTHER PUBLICATIONS

International Search Report of PCT/CA2008/001272, 2007.
Ortho Development engineering simplicity, Balanced Knee System, www.orthodevelopment.com, 2005.
United Orthopedic Corporation, U2 Knee System, Surgical Protocol, www.uoc.com.tw, 2005.

* cited by examiner

*Primary Examiner* — Kevin T Truong
*Assistant Examiner* — David Bates
(74) *Attorney, Agent, or Firm* — Norton Rose Canada LLP

(57) ABSTRACT

A positioning device assembly for positioning a tool guide block for use in an orthopedic surgery on a bone element includes a positioning device having a block body with a reference surface adapted to abut the bone element, and first and second adjustment mechanisms that are independently operable. The first adjustment mechanism permits rotation of a tool guide block about a medial-lateral extending axis such as to provide flexion-extension angle adjustment and the second adjustment mechanism permits rotation of a tool guide block about an anterior-posterior extending axis such as to provide varus-valgus angle adjustment. The second adjustment mechanism includes both a coarse and a fine adjustment mechanism integral therewith. A tool guide block assembly mounted to the positioning device, the tool guide block assembly including a platform portion which is engaged to the block body of the positioning device and the tool guide block which is releasably engaged with the platform.

23 Claims, 15 Drawing Sheets

UNIVERSAL POSITIONING DEVICE FOR ORTHOPEDIC SURGERY AND METHOD OF USE THEREOF

CROSS-REFERENCE TO RELATED APPLICATIONS

The present application is a continuation of International Patent Application No. PCT/CA2008/001272 filed Jul. 9, 2008, which claims priority on U.S. Provisional Patent Application No. 60/948,546 filed Jul. 9, 2007, the entire contents of both which is incorporated herein by reference.

TECHNICAL FIELD

The present invention relates generally to a surgical tool assembly and its method of use in orthopedic knee surgery. More particularly, the present invention is directed to a multiple degree-of-freedom universal positioning device assembly, for use with a computer assisted surgery (CAS) system in total knee replacement surgery.

BACKGROUND OF THE ART

Computer Assisted Surgery (CAS) systems are being increasingly used for orthopedic operations in general, and for joint replacement surgeries in particular, in order to continue to improve the accuracy and long-term success of joint replacement surgery. The accuracy of cuts and drilled holes performed in joint replacement surgeries such as in knee arthroplasty, or total knee replacement, is of prime importance, such that the installation of the implants can be made such that they best duplicate the kinematics of the natural knee.

Known optical, radio frequency and magnetic based CAS systems employ passive and active trackable elements affixed to objects, such as surgical tools and patient bone references, in order to permit the determination of position and orientation of the objects in three-dimensional space. Preoperatively taken images, computer generated models created from pre-operative patient scans or intra operative landmark digitization are some of the methods used to provide accurate patient anatomical information to the CAS system, such that the real-time position of the same anatomical elements can be registered or calibrated and thus tracked by the system, permitting the Total knee replacement surgery, for example, may require one or more precise cuts to be made in the femur and/or tibia to completely remove the knee joint, such that the implant may fit correctly and best replicates the geometry of a natural healthy knee. To perform these steps, in both conventional and CAS total knee replacement surgeries, it is known to use a tool or implement known as a surgical tool guide block which provides a drill and/or cutting guide to assist the surgeon to perform the steps required to prepare the femur and tibia for receiving the implant. For example, using known CAS surgery techniques, the surgical tool guide block, such as a saw cutting guide for example, would be drilled or screwed into that part of the bone to be severed, while in other bone CAS systems, and its position would be determined through known methods using the CAS system.

To best permit the desired positioning and fixation of the surgical tool guide block in the determined position, a surgeon typically uses a positioning block which requires controllable adjustment of several degrees of freedom.

While certain flexibility is provided by such total knee replacement positioning blocks of the prior art, there nevertheless remains a need for an improved positioning device permitting additional control of the adjustment thereof, and being adapted for use with a CAS system.

SUMMARY

It is therefore an object of the invention to provide at least an improved universal positioning device for use in orthopedic surgery.

There is therefore provided, in accordance with one possible aspect, a device for positioning a tool guide block, said device comprising: a positioning device including a block body having an inwardly facing reference surface adapted to abut a bone element, the positioning device including a first adjustment mechanism and a second adjustment mechanism independently operable from the first adjustment mechanism, the first adjustment mechanism permitting rotation of the tool guide block about a medial-lateral extending axis such as to provide flexion-extension angle adjustment, the second adjustment mechanism permitting rotation of the tool guide block about an anterior-posterior extending axis such as to provide varus-valgus angle adjustment, the second adjustment mechanism including a coarse adjustment mechanism and a fine adjustment mechanism; and a tool guide mounted to the positioning device, the tool guide including a platform portion which is engaged to the block body of the positioning device and the tool guide block which is releasably engaged with the platform.

There is also provided, in accordance with another aspect, a device for use in orthopedic knee replacement surgery on a femur, said device comprising: a positioning device including a block body having an inwardly facing reference surface adapted to abut a distal end of the femur, the positioning device including a first adjustment mechanism and a second adjustment mechanism independently operable from the first adjustment mechanism; a tool guide mounted to the positioning device, the tool guide including a platform portion which is engaged to the block body of the positioning device and a tool guide block which is releasably engaged with the platform; and wherein the first adjustment mechanism permits rotation of the tool guide block about a medial-lateral extending axis such as to provide flexion-extension angle adjustment, the second adjustment mechanism permitting rotation of the tool guide block about an anterior-posterior extending axis such as to provide varus-valgus angle adjustment, the second adjustment mechanism including a coarse adjustment mechanism and a fine adjustment mechanism.

There is additionally provided, in accordance with another aspect, a device for use in orthopedic knee replacement surgery on a femur, said device comprising: a positioning device including a block body having a first inwardly facing reference surface adapted to abut a distal end of the femur and a second reference surface adapted to abut a posterior side of the femur, the second reference surface being substantially perpendicular to the first reference surface, the positioning device being positionable relative to the femur without being fastened thereto; a tool guide mounted to the positioning device, the tool guide including a platform portion which is engaged to the block body of the positioning device and a tool guide block which is releasably engaged with the platform via a proximal-distal adjustment mechanism permitting the tool guide block to be displaced relative to the platform, and thus the first inwardly facing reference surface of the positioning device, in a direction substantially perpendicular to the first reference surface, such as to adjust a distal resection depth in the femur; and a varus-valgus adjustment mechanism independently operable from the proximal-distal adjustment mechanism and provided in the block body of the positioning device for adjustment of a varus-valgus angle of the block body relative to the femur and therefore the varus-valgus angle of the tool guide block mounted to the positioning device.

There is further provided, in accordance with another aspect a method of installing a tool guide block on a knee bone element in preparation of a cut to be performed in the knee bone element during orthopedic knee replacement surgery, the tool guide block being engaged to a positioning device, the method comprising: abutting a first reference surface of the positioning device against the knee bone element; determining a desired position and orientation of the tool guide block relative to the knee bone element; adjusting at least one of a positioning and orientation of the positioning device until the tool guide block engaged thereto is in said desired position and orientation, the step of adjusting comprising: adjusting a flexion-extension angle of the tool guide block while maintaining the first reference surface abutted against the knee bone element; independently adjusting a varus-valgus angle of the tool guide block by first making a coarse adjustment and then making a fine adjustment; adjusting a distal resection depth by displacing the tool guide block relative to the positioning device; locking the positioning device in position such as to maintain the adjusted flexion-extension angle, varus-valgus angle, and distal resection depth of the tool guide block; and fastening the tool guide block in place to the knee bone element once the desired position and orientation of the tool guide block has been reached.

BRIEF DESCRIPTION OF THE DRAWINGS

Further features and advantages of the present invention will become apparent from the following detailed description, taken in combination with the appended drawings, in which.

DETAILED DESCRIPTION OF A PREFERRED EMBODIMENT

Figure 1:
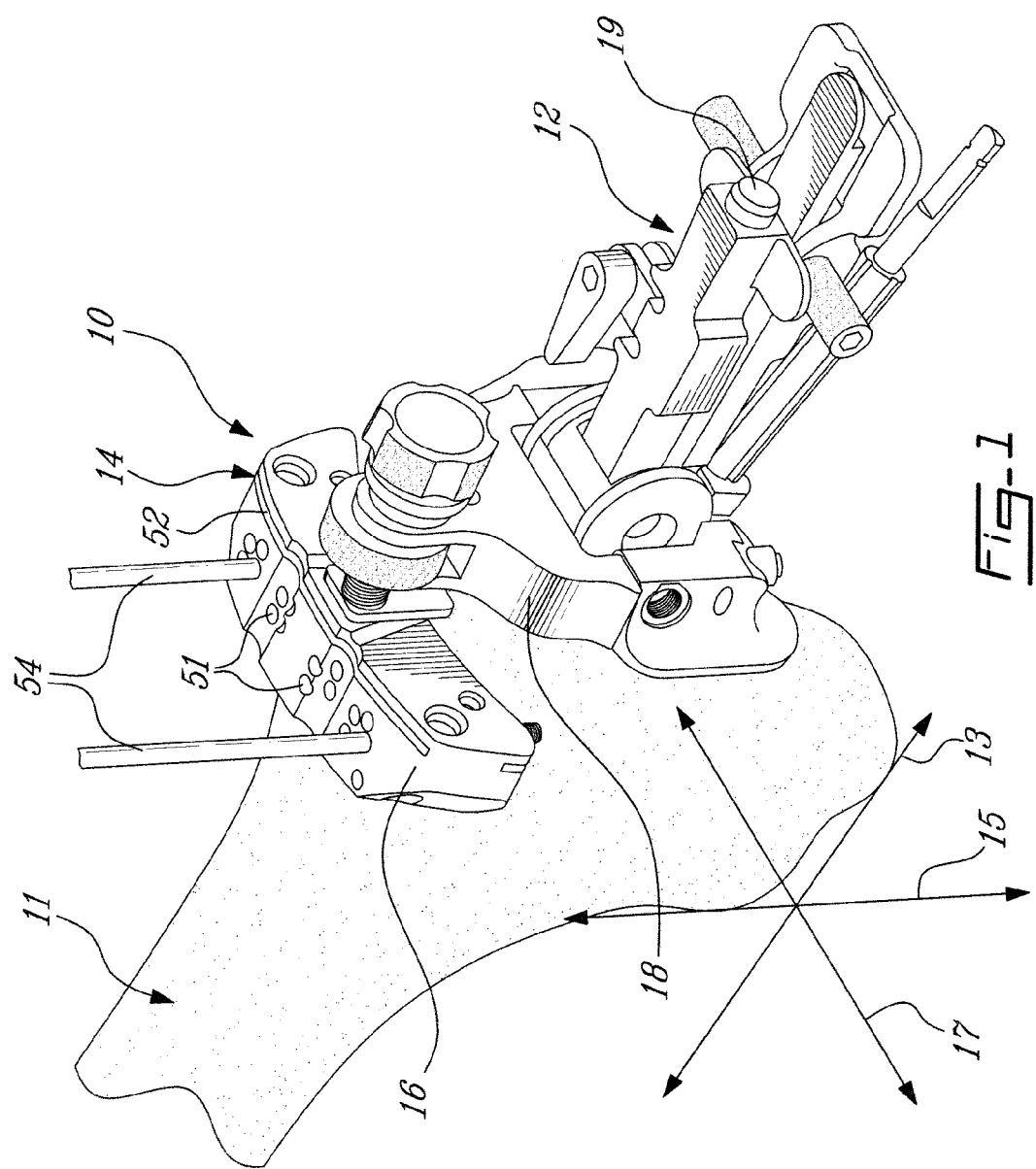
FIG. 1 is a perspective view of a universal positioning device assembly in accordance with one aspect of the present invention, shown mounted to a femur, the universal positioning device assembly including a positioning device and a tool guide block assembly engaged thereto.

As seen in FIG. 1, a device 10 for use in orthopedic surgery includes generally a positioning device 12 and a tool guide 14 which is mounted thereto. The tool guide 14 includes a platform portion 18 which is engaged to the positioning device 12, and a tool guide block 16 which is releasably engaged with the platform 18 and is displaceable relative thereto in a controlled manner and in at least one degree of freedom. Preferably, although not necessarily, the platform 18 of the tool guide 14 is also releasably engaged to the positioning device 12, i.e. such that the platform 18 and the positioning device 12 can be disconnected from each other. However, the tool guide block 16 is necessarily disengageable from the platform 18 and thus the rest of the device 10. As will be discussed below, the positioning device 12 and the platform 18 permit adjustment of the relative position between the tool guide block 16 and the bone element in multiple degrees of freedom, such that the tool guide block 16 can be accurately positioned into a desired location relative to the bone element. As will be described, the positioning device 12 of the device 10 is removably fastened to the bone element, such as the femur 11 shown in FIG. 1, using a bone anchor such as a spike 19.

The device 10 will be described in detail below. The device 10 may however also include certain additional features, or be used in a similar manner or in accordance with a surgical method, as per those devices described in Applicant's own U.S. patent application Ser. Nos. 10/357,493, 11/062,737 and 11/042,264, respectively filed on Feb. 4, 2003, Feb. 23, 2005 and Jan. 25, 2005, the entire contents of each of which are incorporated herein by reference. These three applications were published as US patent application publications nos. 2004/0039396, 2005/0203528 and 2006/0195111, respectively.

Throughout this application, the general device 10 described and depicted herein will be alternately referred to as a device, a universal positioning device, or universal positioning device assembly, a positioning device assembly or positioning block assembly, and it is understood that all of these terms refer to the device 10, which is intended for use in orthopedic surgery, such as for example, total or partial joint replacement surgery of the knee, elbow, hip, shoulder or other joint, unicondylar osteotomy, unicompartmental knee replacement, total knee arthroplasty, high tibial osteotomy, etc. The present device 10 will be described herein with specific reference to its use in orthopedic knee surgery (such as a total knee replacement for example), and more particularly with respect to its use and installation on a femur 11 of a knee joint. However, it is to be understood that the present device 10 can be similarly used on a tibia, also during a knee joint surgery such as a total knee replacement, or alternately still on another bone element of a patient, such as a bone of an elbow, hip, shoulder or other joint for example.

In the embodiment described herein, the directions of displacement of the device 10 will be described with respect to a coordinate system defined relative to a femur 11, to which the assembly is installed in the depicted embodiment. As shown in FIG. 1, this Cartesian coordinate system is defined by a Proximate-Distal axis 13, an Anterior-Posterior axis 15, and a Medial-Lateral axis 17.

Such positioning devices as sometime referred to by those skilled in the art as "positioning blocks" or "universal positioning blocks", however it is to be understood that such devices need not actually include a "block" shaped portion per se. Furthermore, the positioning block assembly may be used in conjunction with a computer assisted surgical (CAS) system or may be used on its own, i.e. in a standard or non-CAS surgical environment.

The universal positioning device comprises a main positioning device or guide block holder that is operatively engaged, in a releasable manner, with a surgical tool guide block assembly that includes the tool guide block. The positioning device is adapted to accurately position and align the tool guide block into a desired location. The surgical tool guide block is adapted for guiding a surgical tool and it is to be understood that such a surgical tool as defined herein includes all surgical instruments necessary for bone surgery and joint replacement surgery, for example those which can remove bone from a bone element, such as drills, rasps and saws and that such a surgical tool guide block is similarly adapted for any surgical instrument necessary for joint replacement surgery, for example those which can remove bone from a bone element. For example, the tool guide block may be used to guide a surgical saw used to make a resection cut in the bone element and/or used to create a hole therein using a surgical drill. It may be further understood that the surgical tool guide block may also be a surgical device itself.

As noted above, the universal positioning device assembly may used in conjunction with a CAS system, and thus may be trackable by the CAS system, which provides means for determining the position, orientation and movement of the universal positioning device assembly in three dimensional space, and permits the universal positioning device assembly to be visualized, for example using a display, relative to the patient anatomy. The CAS system further provides means for determining a desired position of the universal positioning device assembly relative to a bone element, whether from a real patient, a cadaver or a model. The CAS system further provides means for indicating where to fasten the surgical tool guide block on such a bone element such that it can be affixed into the desired position. Additionally, the present universal positioning device assembly may be used with both CT-based and image-less CAS systems or fluoroscopic systems. The CAS system may, in other words, use either computer generated anatomical models created from pre-operatively taken scans, such as CT scans, or use intra-operatively generated bone surface models created by digitizing a plurality of points and anatomic landmarks on the surface of the bone element, to relate the position of the positioning block assembly to the bone elements of the patient.

Figure 2:
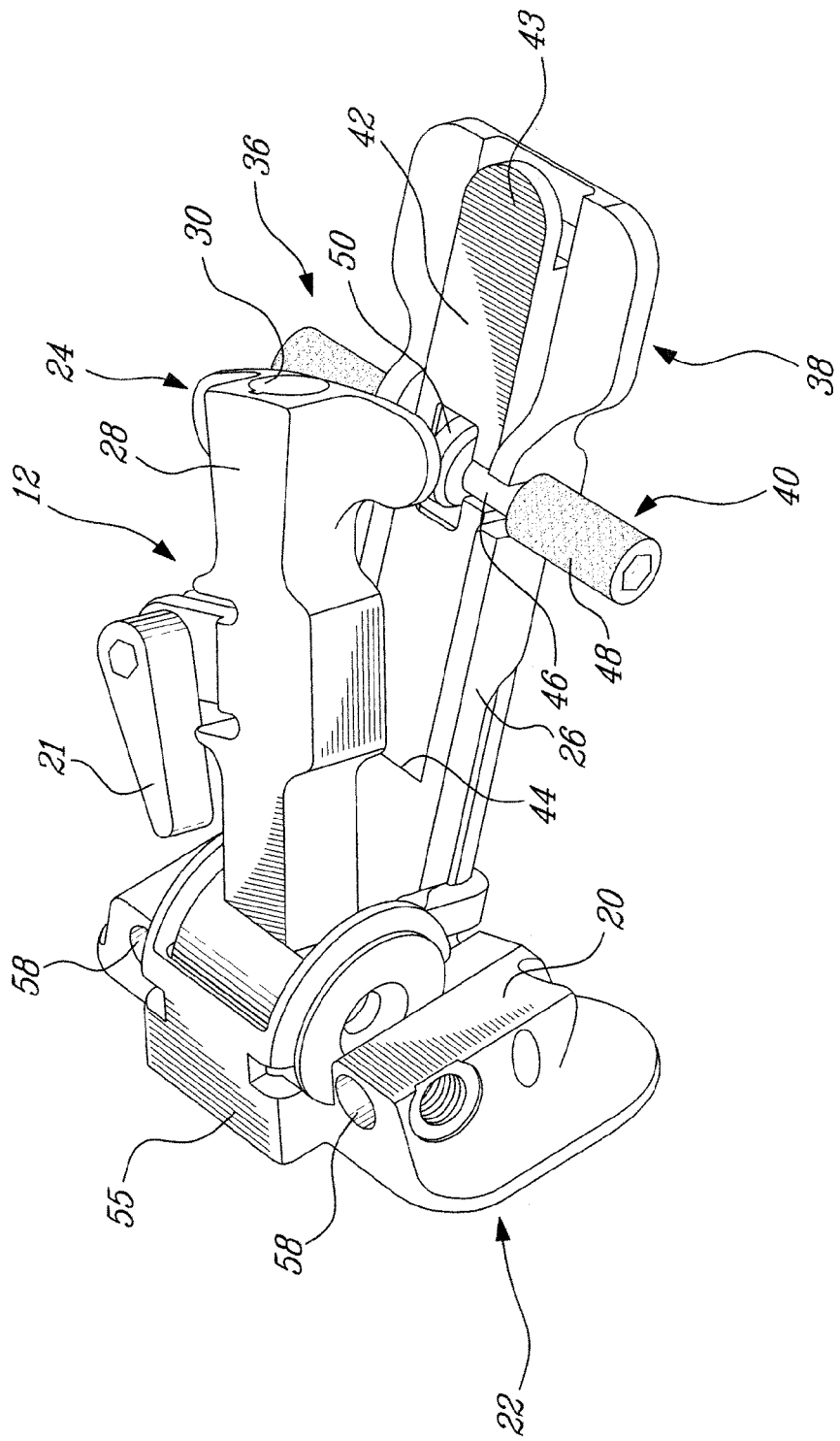
FIG. 2 is a perspective view of the positioning device of the assembly of FIG. 1.
Figure 3:
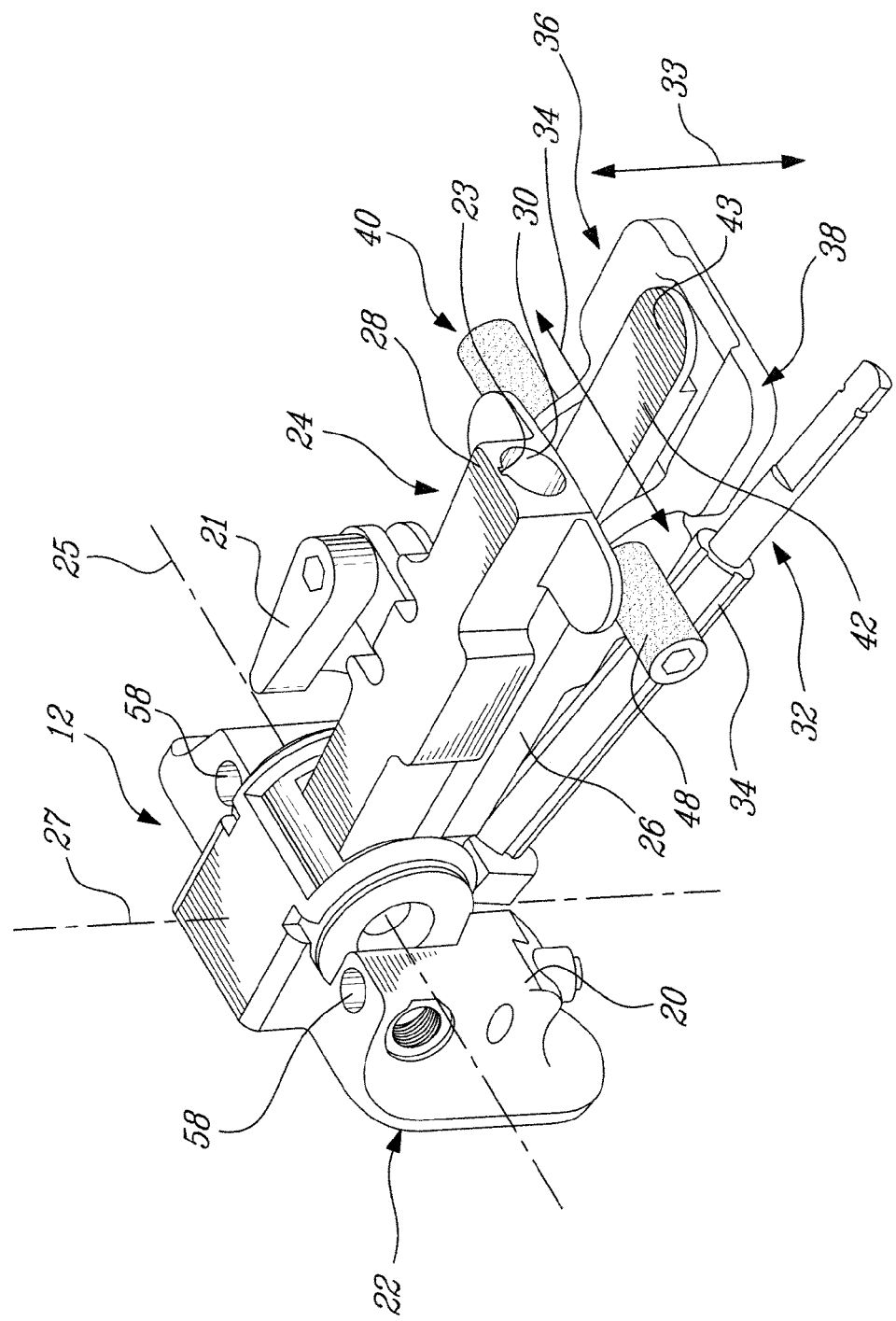
FIG. 3 is another perspective view of the positioning device of the assembly of FIG. 1.

Referring to FIGS. 2-3, the positioning device 12 of the universal positioning device 10 is shown in greater detail. The positioning device 12 includes a main block body 20 which has a substantially planar reference surface 22 on one side thereof, namely on a proximally-facing side when the positioning device 12 is being installed onto a distal end of a femur. It is this planar reference surface 22 which abuts the distal condyle(s) of the femur when the device is installed in place, as will be described in further detail below. A swing arm member 24 is pivotally engaged to the block body 20 and extends away therefrom in a substantially distal direction. The swing arm member 24 includes a first portion 26 and a second portion 28, which pivot together relative to the block body 20 about a first pivot axis 25, which is adapted to be substantially parallel to the medial-lateral axis 17 (see FIG. 1) when the positioning device 12 is mounted in position on the bone element, such as the femur 11. This is preferably done using a bone anchor in the form of a spike 19 (see FIGS. 1 and 4), which is received through a correspondingly shaped passage 30 that extends through the length of the second portion 28 of the arm member 24. The entire positioning device 12 is thus slid onto the spike 19, preferably until the reference surface 22 thereof is abutted against the femur 11. The positioning device 12 is fixed in place on the spike 19 by a locking mechanism, including a locking lever 21, which is pivotable between a locked and an unlocked position. The locking lever 21 is engaged with a friction clamp which is disposed within the arm member 24 and protrudes into the passage 30 therethrough, such as to frictionally engaged the spike 19, thereby locking the positioning device 12 in place at a selected point along the spike. In one embodiment, the spike 19 is provided with a small pin 76 thereon, and the arm member 24 includes a correspondingly shaped channel 23 in communication with the passage 30, such that when the pin 76 of the spike 19 and the channel 23 of the arm member 24 are interlocked, the positioning device 12 is prevented from rotating (i.e. about a longitudinal axis of the spike) on the spike 19. Alternately, of course, the spike could be provided with a non-circular cross-sectional area and/or shape (such as cross shaped for example), and the passage 30 could be similarly shaped, in such case the cooperating pin and channel are no longer required. Also, if preferred by the surgeon such as to be able to manually alter the relative angular orientation of the positioning device 12 on the spike 12 (i.e. about a longitudinal axis of the spike), a spike 19 without such a pin thereon can be used.

The first portion 26 of the swing arm member 24 comprises a lower platform portion which can only pivot about the first axis 25 relative to the block body 20. The second portion 28, which rest on top of the lower platform portion 26, comprises a main arm body, through which the passage 30 extends. This arm body 28 pivots relative to the block body 20 together with the lower platform portion 26 about the first pivot axis 25, however also pivots in a second, substantially perpendicular direction, namely about a second pivot axis 27 which is substantially parallel to the anterior-posterior axis 15. This is achieved by a pivoting joint between the arm body 28 and the lower platform portion 26.

Thus, if one were to hold the block body 20 stationary, the entire arm member 24 could be pivotally displaced, about the medial-lateral extending first pivot axis 25, in a first direction 33, which will be defined herein as a flexion-extension direction or adjustment of the flexion-extension angle, and the arm body portion 28 of the arm member 24 would also able to be displaced in a second direction 34, which will be defined herein as a varus-valgus direction or adjustment of the varus-valgus angle. However, in use, as it is the arm body portion 28 which has the spike passage 30 therethrough, it is this portion of the assembly which remains substantially stationary relative to the femur 11 when the positioning device 12 is slid onto the spike 19 in the femur. Thus, when so mounted on the bone spike 19, it is the block body 20 which is displaced (relative to the arm body 28 and thus relative to the bone) in the flexion-extension direction 33 and/or the varus-valgus direction 34. As such, this permits adjustment of flexion-extension angle and the varus-valgus angle of the block body 20, and therefore of the planar reference surface 22 thereof. As will be described, the displacement of the block body 20 in these two angular directions is controlled using independent adjustment mechanisms.

As noted, relative pivotal movement between the block body 20 and the swing arm 24 about the medial-lateral extending axis 25 is achieved by a pivot joint therebetween. Adjustment of this relative flexion-extension angle is achieved using a lockable adjustment handle 32 (see FIG. 3) which is mounted to the block body 20 and extends therefrom below the pivoting arm member 24. The handle 32 is fixed to the block body 20, and extends through an opening in a projection of the arm member 24 on the platform portion 26. A rotating locking nut 34 is threadably engaged to the handle 32, and when tightened, the locking nut 34 is displaced down the length of the handle 32 towards the block body 20, and acts to clamp the arm member 24 in a fixed pivotal position about the first pivot axis 25, relative to the block body 20. This permits the flexion-extension angle to be fixed at a desired value. Practically, this may be best achieved by applying a little friction by first lightly tightening the locking nut 34, permitting the block to be roughly positioned in the desired flexion-extension orientation. Then, by manipulating the handle 32, the finer tuned positioning of the block can be done. Once a final orientation is reached, the locking nut 34 can be fully tightened to fix the block in place.

With the arm member 24 fixed in position in the flexion-extension direction 33, the block body 20 remains free to be pivotably displaced about the second pivot axis 27, such as to adjust the varus-valgus angle in direction 34. This is achieved using an adjustment mechanism 36 between the platform portion 26 and the arm body 28 of the member 24, which permits both course and fine adjustment of the varus-valgus angle of the platform portion 26 of the arm member 24, and therefore of the block body 20 connected thereto, relative to stationary upper arm body 28 fixed to the spike 19 (and thus fixed relative to the femur 11).

The varus-valgus adjustment mechanism 36 includes a coarse adjustment mechanism 38 and a fine adjustment mechanism 40. The coarse adjustment mechanism 38 including a central tab or fork 42 which is cantilevered from the remainder of the platform portion 26 at proximal joint 44, such that it has a free distal end 43 which can be depressed by a user. The tab 42 is biased upwards towards the arm body 28 such that a pinion gear 50 which is mounted to the tab 42 is normally engaged to a corresponding "rack" (not shown) which is formed on the underside of the arm body 28. Thus, the sprung tab is biased such that the two portions of the arm member 24, namely the arm body 28 and the platform portion 26, are engaged together such as to substantially prevent (unless the fine adjustment mechanism 40 is actuated as will be described below) relative movement therebetween in the varus-valgus angular direction 40. This is achieved by the engagement of the pinion gear 50 and the associated rack (which make up part of the fine adjustment mechanism 40, which interlock to prevent coarse (or large) relative movement between the two portions of the arm member 24. However, when the distal end 43 of the sprung tab 42 of the platform portion 26 is depressed by a user, the tab 42 is pivoted away from the arm body 28 which thereby disengaged the pinion gear 50 from the corresponding rack on the arm body. This accordingly permits rapid and large (but coarse) relative pivotal movement between the arm body 28 and the platform portion 26 about the second pivot axis 27. Thus, the coarse adjustment mechanism 38 enables the user to quickly and easily position the block body 20 into a rough position corresponding to the desired varus-valgus angle between the reference surface 22 of the block body 20 and the bone element (e.g. the femur).

The fine adjustment mechanism 40 can then be used in order to fine-tune the exact varus-valgus angle desired. The fine adjustment mechanism 40 includes the pinion gear 50 as noted above, the pinion gear 50 being fixed to a shaft 46 that is rotatably mounted to the tab 42 of the platform portion 26. At each opposed end of the shaft 46 is provided a screw knob 48. Accordingly, by rotating the screw knobs 38 in either direction, pinion gear 50 (which is in engagement with the rack given the coarse adjustment mechanism 38 is no longer actuated) is displaced relative to the fixed rack on the arm body 28 in the direction 34, thereby displacing the platform portion 26 in relatively small increments in this direction, thereby permitting the exact value of the varus-valgus angle to be adjusted.

Although the adjustment mechanism 36, which includes the integrated coarse adjustment mechanism 38 and the fine adjustment mechanism 40, has been described above particularly with its use for adjusting the varus-valgus angle of the device, it is also to be understood that the positioning device 12 can be configured such that this type of coarse and fine adjustment mechanism 36 can also be provided for the adjustment of the flexion-extension angle in stead of the simpler pivoting adjustment described above, and this either in addition to or instead of the adjustment mechanism 36 used for the varus-valgus angle adjustment.

Figure 5:
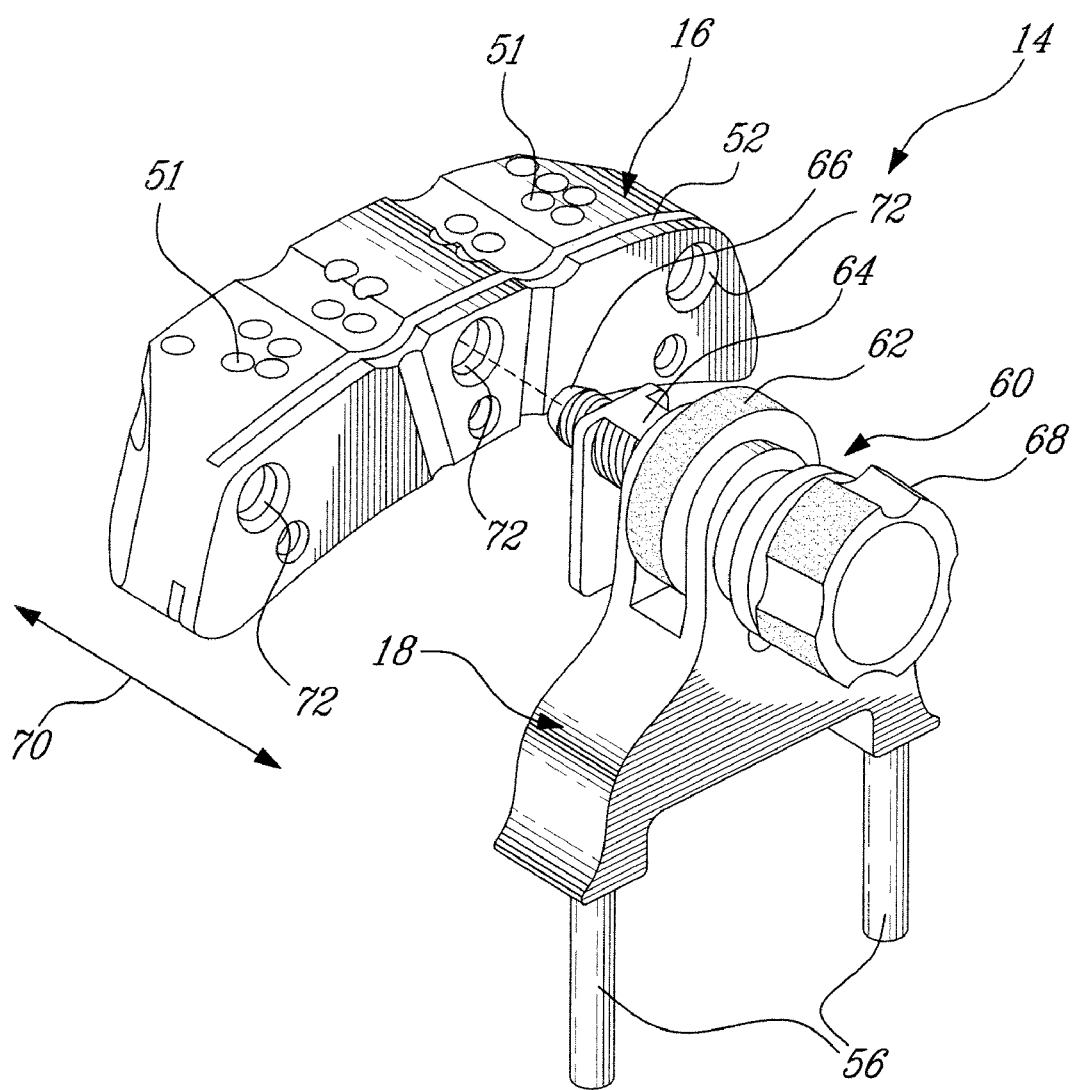
FIG. 5 is a perspective view of a tool guide block assembly which mounts to the positioning device of FIG. 3.

Now that the positioning device 12 of the universal positioning device 10 has been described, the other portion of the assembly, namely the tool guide 14, will now be discussed. Referring to FIG. 1 and FIG. 5, the tool guide 14 includes generally a platform 18 and a tool guide block 16 mounted thereto. The tool guide block 16 is that which is used by the surgeon to create a cut, a hole, etc in the bone element being operated on, such as the femur described herein. The tool guide block 16 thus may include one or more of a cutting guide slot, a drilling guide hole, pin guide holes and the like, or any combination thereof. In one example, the tool guide block 16 is used to make a resection cut in a distal end of a femur, such as during a knee replacement surgery. Typically, and as will be described further below, once the guide block 16 is located in a desired position on the femur 11 with the aid of the positioning device 12, holes are then drilled into the bone using the guide holes 51 in the guide block 16 and pins 54 (see FIG. 1 for example) are inserted therethrough such as to pin the guide block 16 to the femur in this desired location. A resection cut can then be made at the desired location and angle in the femur, using for example a saw blade guide slot 52 located in the guide block 16.

The platform 18 includes two downwardly extending legs 56, which are received within two correspondingly shaped openings 58 defined in the block body 20 of the positioning device 12 (see FIGS. 2-3). Thus, the platform 18 is removably engaged to the block body 20 of the positioning device 12 by inserting the legs 56 into the openings 58, and then sliding the platform down into abutting engagement with an anterior surface 55 on the proximal end of the positioning device. The platform 18 includes a threaded adjustment mechanism 60, which includes a rotating adjustment knob 62 which actuates the threaded shaft 64 of the mechanism to rotate, thereby rotating the captive shaft 64 and thus translating the tool guide block 16, which is engaged to a free end 66 of the shaft 64, in a proximal-distal direction 70. The adjustment mechanism 60 thus provides for adjustment of a distal resection distance in a total knee replacement operation (i.e. the distance in a proximal direction away from the distal most point on the femoral condyles—to which the reference surface 22 of the block body 20 is abutted—which is desired such that the distal resection cut to be made in the femur is located in a desired position).

As noted above, the platform 18 is disengageable from the tool guide block 16, such that once the tool guide block 16 is located in a desired location relative to the bone element, it can be pinned in place thereto and the platform 18 (and accordingly the rest of the universal positioning device assembly 10) can be unfastened from the tool guide block 16 and removed from engagement with the bone. Accordingly, by unscrewing the un-coupling knob 68, the threaded shaft 64 is disengaged and withdrawn from the threaded aperture 72 in the guide block 16 to which it was received.

As best seen in FIG. 5, the tool guide block 16 includes several different apertures 72 therein with which the free end 66 of the threaded shaft 64 can be matingly engaged. More particularly, in the depicted embodiment, three such apertures 72 are provided, namely one centrally located aperture and one aperture located on each of the opposed lateral ends of the substantially elongated tool guide block 16. This provides an improved range of possible locations of the tool guide block 16 relative to the bone to which is being positioned. For example, when on a femur 11 in a knee replacement surgery, this permits an increased number of resection cuts to be possible using the present assembly, such as both from an anterior direction and from either a more medial or lateral direction. This provides improved flexibility of positioning of the tool guide block 16, relative to many prior art structures for example which only permit engagement of a tool guide block at a single, typically, central location thereto.

Having generally described the structure of the universal positioning device assembly 10, a method of use thereof will now be described with reference to performing a distal resection cut in a femur during a total knee replacement surgery. The steps performed in accordance with this method are those for positioning the tool guide block in preparation of performing a distal cut in the femur in accordance with a so-called "distal cut first" surgical procedure, however as noted above it is to be understood that the universal positioning device assembly 10 can also be used with the alternate "anterior cut first" procedure of preparing the femur for the installation of a femoral implant in a knee replacement surgery.

Reference will now be made to FIGS. 6-22 which depict the successive steps employed in using the universal positioning device assembly 10 for positioning the tool guide block 16 on the femur in preparation of making a distal resection cut in a femur 11 in preparation for the femur receiving an implant as part of a total knee replacement surgical procedure.

Figure 4:
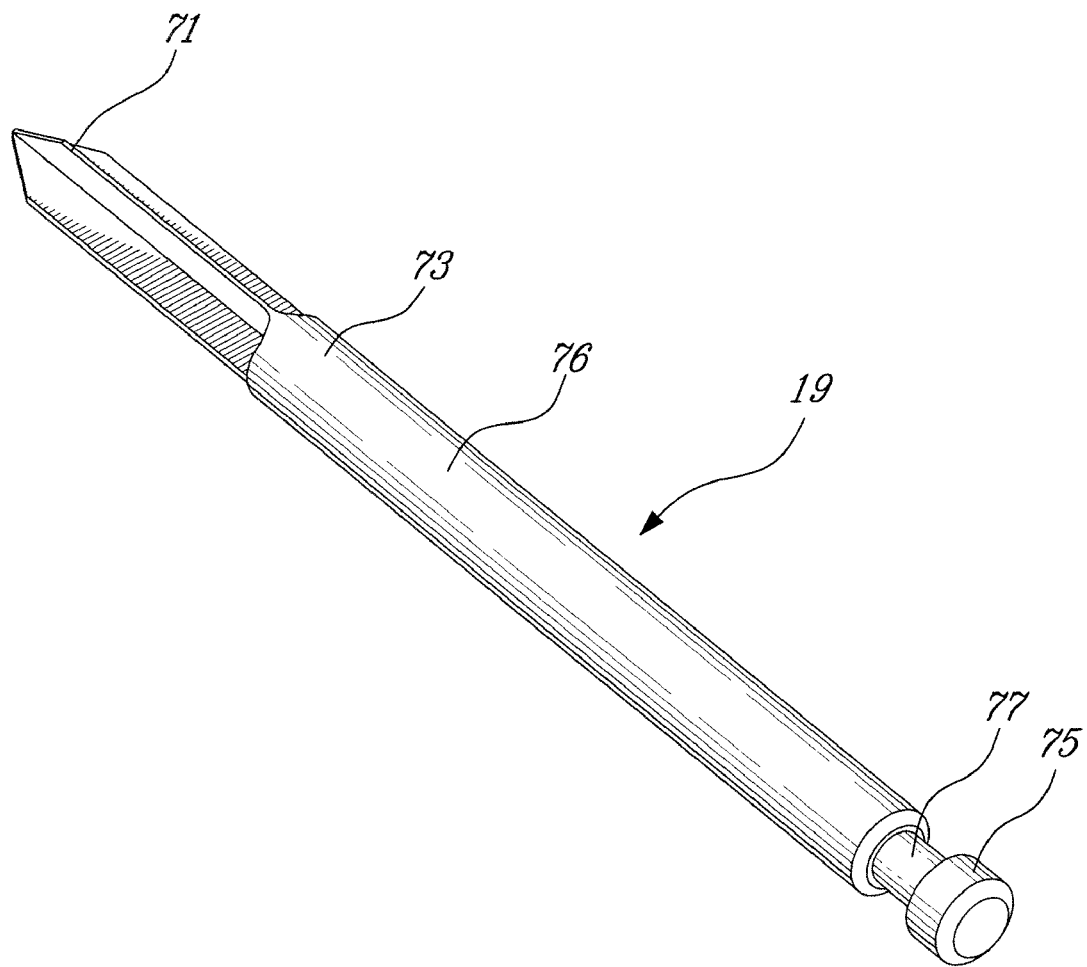
FIG. 4 is a perspective view of a locating spike used to fasten the positioning device to a bone element.
Figure 6:
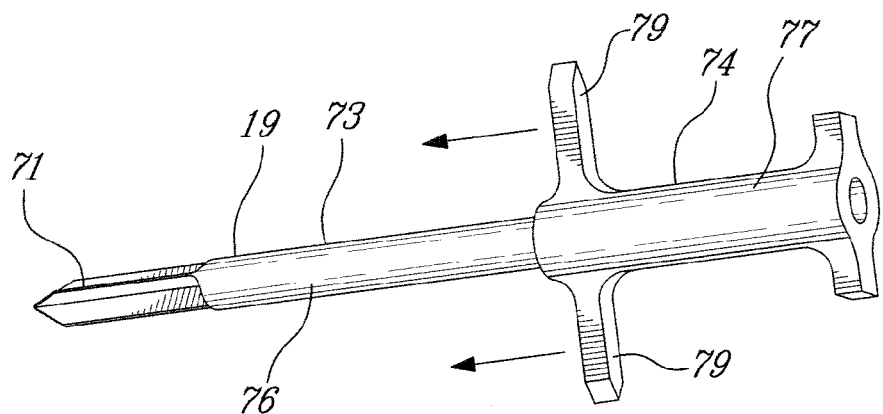
FIG. 6 is a perspective view of the locating spike with a rotation guide used for the installation of the locating spike.

FIG. 6 shows a first step of sliding a rotation guide 74 onto a distal end of a spike 19, such as that described above and shown in FIG. 4. The spike 19 acts as a bone anchor and includes, as best seen in FIG. 4, a sharp and pointed proximal end 71 for being driven into the femur 11, a substantially smooth cylindrical body 73 and a distal end 75 with a groove 77 therein. As seen in FIG. 6, the rotation guide 74 is slid onto the distal end 75 of the spike 19, such that the small pin 76 (which radially projects from the surface of the spike's body 73) is received within a correspondingly shaped channel 77 formed along the length of the rotation guide 74, thus preventing relative rotation between the spike 19 and the rotation guide 74.

Figure 7:
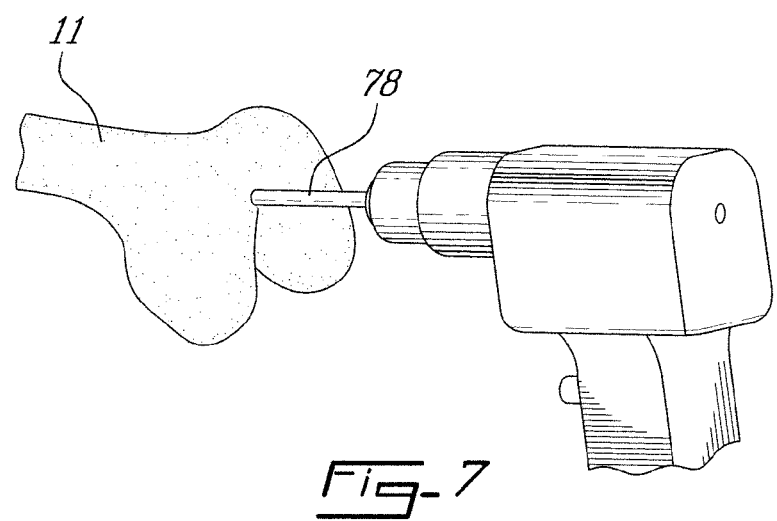
FIG. 7 is a perspective view of a drill piercing a hole at a desired location of the femur.

As shown in FIG. 7, the bone cortex is then broken at the distal end of the femur 11, using a drill bit 78 for example, or alternately a cortex breaker. This hole in the femur 11 is created at the exit point of the mechanical axis of the femur.

Figure 8:
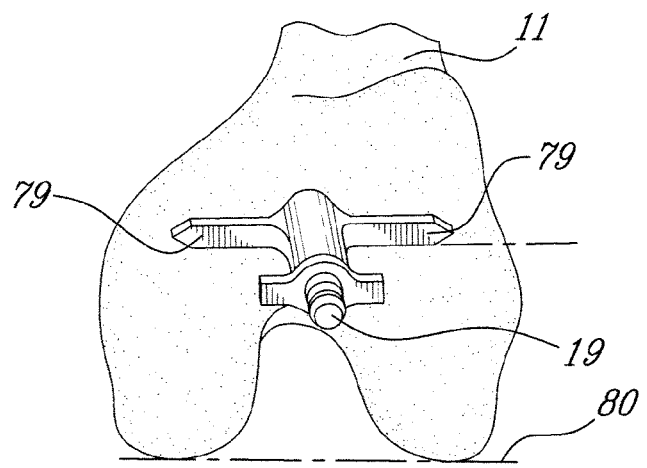
FIG. 8 is an end view of the locating spike inserted into the hole created in the femur using the rotation guide.

FIG. 8 shows the next step, which is to align the two laterally projecting guide arms 79 of the rotation guide 74 such that they are substantially parallel with the femoral posterior axis 80, i.e. an axis passing through the two most posterior points of the femoral condyles.

Figure 9:
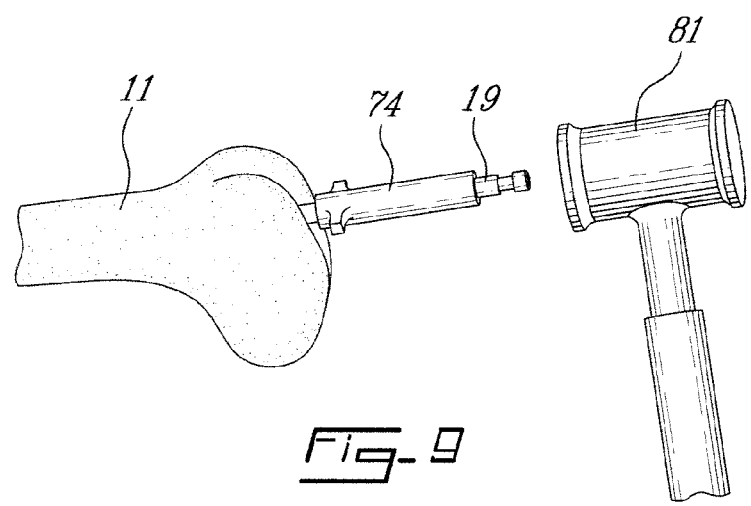
FIG. 9 is a side view of the locating spike being impacted into the femur using a mallet.

The next step, shown in FIG. 9, is to insert the shaft proximal end 71 of the spike 19 into the hole created in the distal end of the femur 11, with the laterally projecting guide arms 79 still in alignment with the femoral posterior axis. The spike 19 can then be impacted into the femur a desired distance, using an impact mallet 81 for example. The spike should be securely embedded into the femur 11 such that no play exists, however should only be impacted to a maximum depth which is marked on the spike 19. This may correspond to the length of the four cross-shaped blades of the sharp proximal end 71 of the spike 19.

Figure 10:
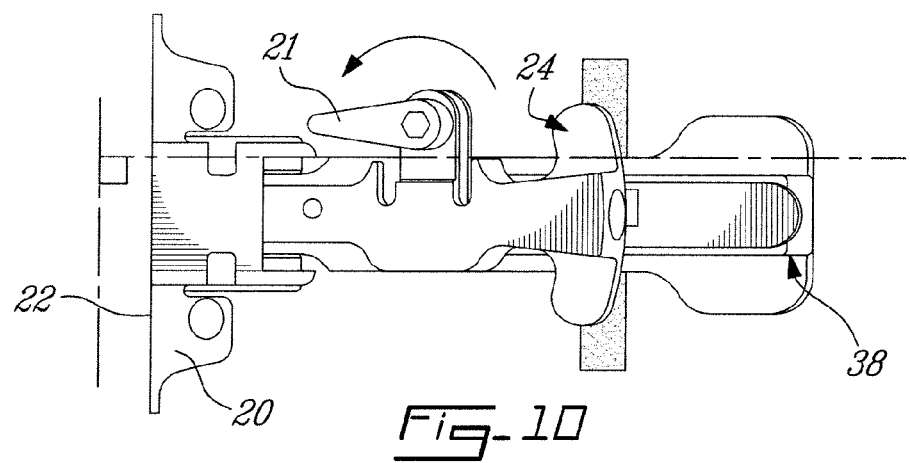
FIG. 10 is a top plan view of the positioning device which is aligned with a varus-valgus axis.
Figure 11:
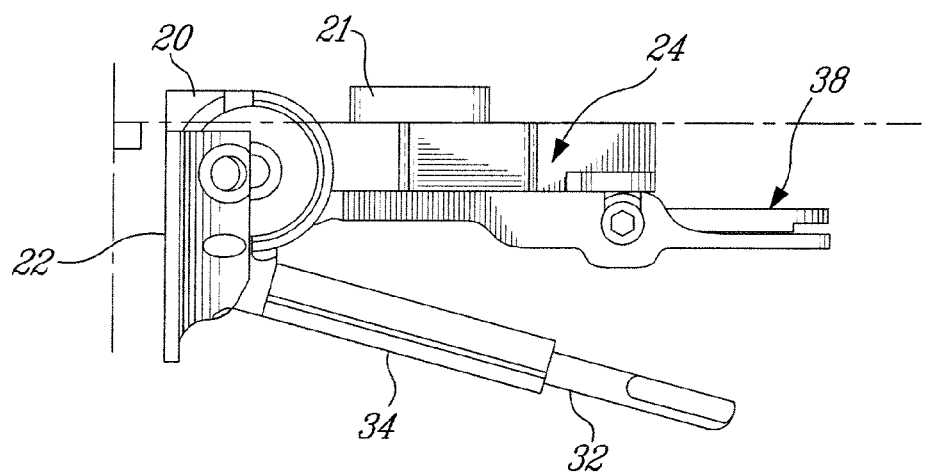
FIG. 11 is a side elevation view of the positioning device which is aligned with a flexion-extension axis.

Referring now to FIGS. 10 and 11, the positioning device 12 as described above is then preferably pre-aligned in a neutral position, such as to save the surgeon time with subsequently making the femoral adjustments. This is done by aligning the varus-valgus angle, i.e. between the reference surface 22 of the block body 20 and the arm member 24, at 0 degrees as shown in FIG. 10, such as by using the coarse adjustment mechanism 38 in the manner described above. The flexion-extension angle between the reference surface 22 of the block body 20 and the arm member 24 is also then pre-aligned at 0 degrees, as shown in FIG. 11, such as by using the adjustment handle 32 and associated locking nut 34 in the manner described above. In preparation of being mounted to the spike, the locking lever 21 is also preferably rotated into its unlocked position, as depicted in FIG. 10.

Figure 12:
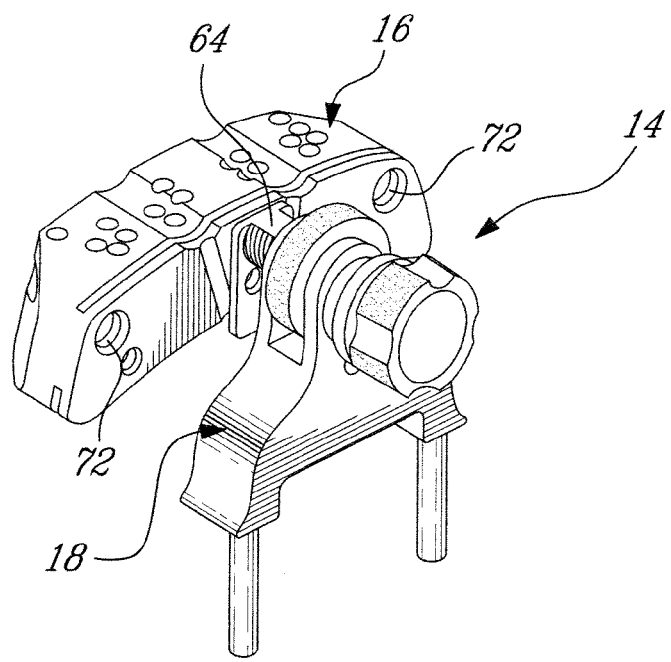
FIG. 12 is a perspective view of the tool guide block assembly of FIG. 1.

As shown in FIG. 12, if it has not already been done, the tool guide block 16 is engaged to the platform 18, such as to assembly the tool guide 14. Any one of the various apertures 72 in the guide block 16 may be used for mating engagement with the threaded shaft 64, however typically the central one is first chosen, as shown in FIG. 12.

Figure 13:
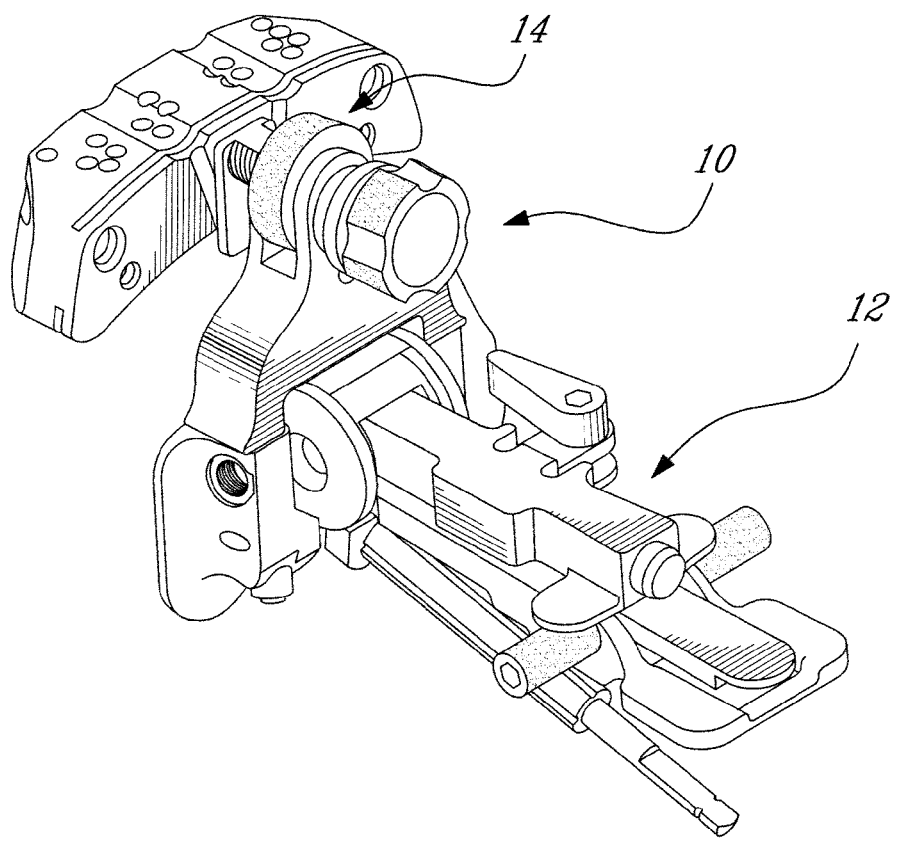
FIG. 13 is a perspective view of the positioning device and the tool guide block assembly assembled together ready for installation.

The now assembled tool guide 14 can then be mounted onto the positioning device 12, in a manner described above, such as to arrive at the complete device 10. The fully assembled universal positioning device 10 is shown in FIG. 13.

Figure 14:
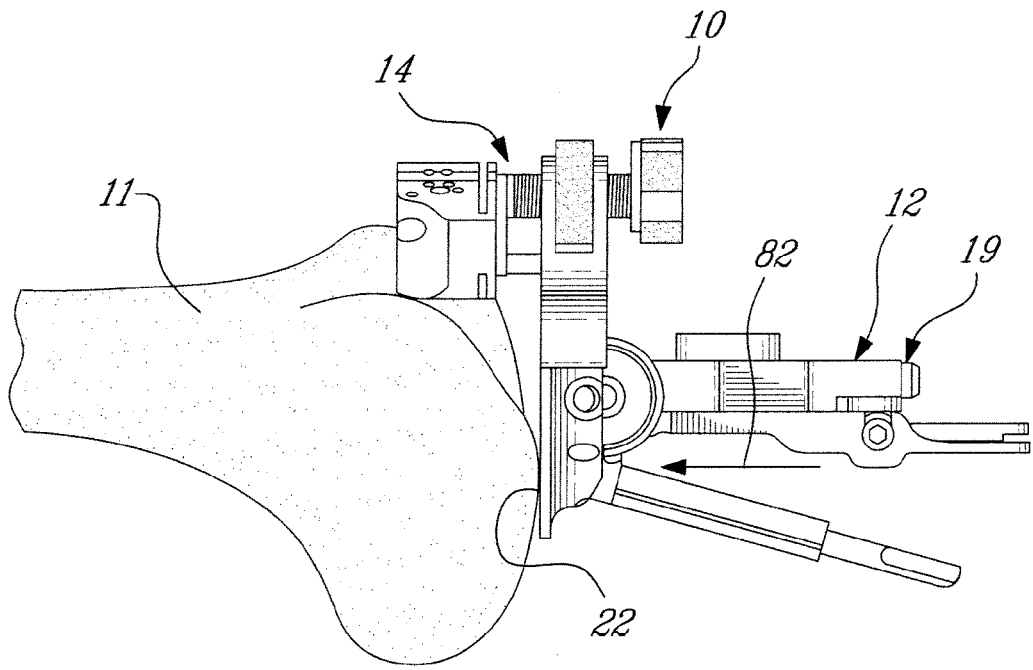
FIG. 14 is a side view of the universal positioning device assembly being installed in place on the locating spike such that the planar surface of the alignment guide is abutted against the distal end of the femur.

As seen in FIG. 14, the universal positioning device 10 is then slid onto the spike 19, by inserting the distal end 75 of the spike 19 into the passage 30 defined in the arm body 28 of the positioning device 12, as described above. Care should be taken to align the anti-rotation pin 76 of the spike with the channel 23 defined in the arm body 28 of the positioning device 10, as noted above, in order to prevent unwanted rotation of the entire assembly 10 about the longitudinal axis of the spike 19. The universal positioning device assembly 10 is slid fully down the spike 19 in the proximal direction 82, until the planar reference surface 22 of the block body 20 directly abuts the distal most point on either of the condyles of the femur. Once in place, the locking lever 21 may, if desired, be moved into its locked position such as to locate the positioning device in place (in the proximal-distal direction) on the spike 19.

The adjustment of the flexion-extension angle and the varus-valgus angle is now performed, such to achieve the desired values thereof which may be provided by, or determined with the aid of, a CAS system. The desired values of these angles will correspond to those which will result in a desired final position and orientation of the tool guide block 16, such as to permit a distal resection cut in the desired location and orientation.

Figure 15:
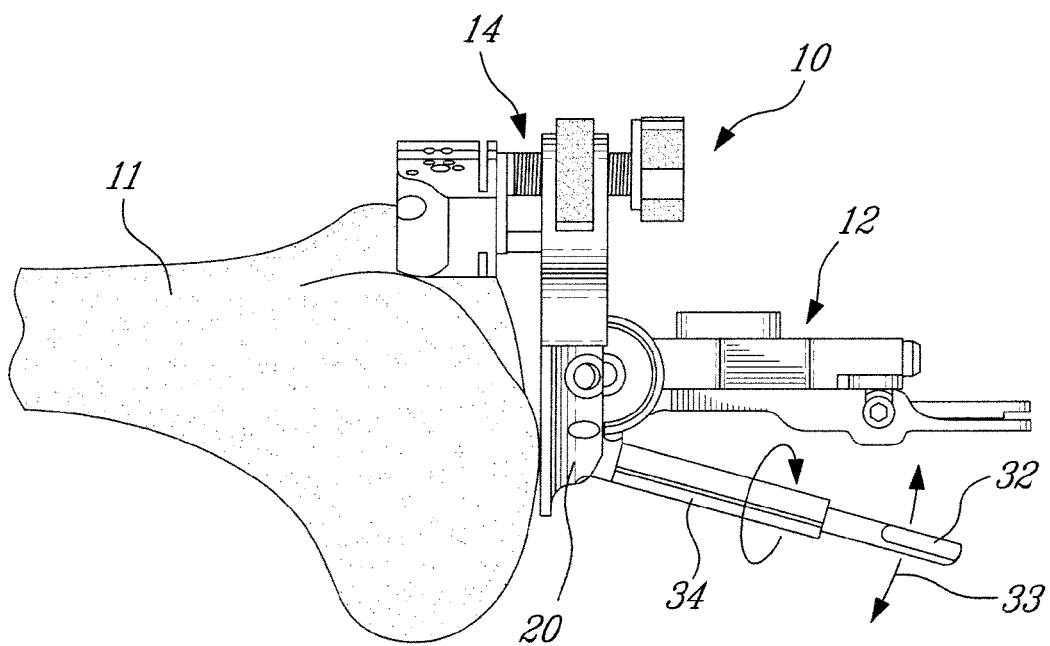
FIG. 15 is a side view of the universal positioning device assembly mounted on the femur, showing the flexion-extension angle being adjusted and fixed using the lockable handle of the positioning device.

As seen in FIG. 15, the flexion-extension angle is preferably first adjusted, using the adjustment handle 32 described above. For example, the handle 32 is manipulated in the direction 33, with a slight friction applied by the locking nut 34, such as to pivot the block body 20 (and therefore the tool guide assembly 14 mounted thereto) about the pivot axis 25, thereby varying the flexion-extension angle thereof, in the manner described in more detail above. Once in the final position corresponding to the desired flexion-extension angle, the locking nut 34 is rotated as shown to lock the device in this angular position.

Figure 16:
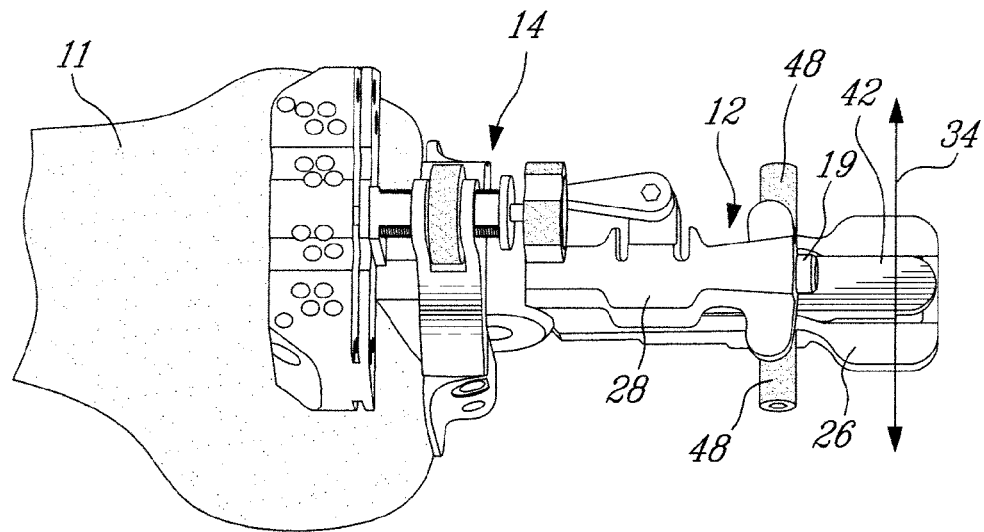
FIG. 16 is a top view of the universal positioning device assembly mounted to the femur, showing adjustment of the varus-valgus angle.

As shown in FIG. 16, the varus-valgus adjustment is then performed, in the manner described above, using the adjustment mechanism 36 of the positioning device 12. Generally, coarse adjustment of the varus-valgus angle is made by depressing the tab 42 and sliding the platform portion 26 in the direction 34 relative to the stationary arm body 28 fixed to the spike 19. Once the desired location is reached, releasing the tab 42 will cause the rack and pinion mechanism of the fine adjustment mechanism 40 to re-engage. The rack and pinion mechanism may be configured such that pre-defined increments of known amounts (ex: 1 degree steps) can be felt by the user when displacing the platform portion 26 during the coarse adjustment. Fine tuning of the exact varus-valgus angle (ex: for values between full degree steps) can then be performed by rotating the screw knobs 48 which rotate the captive pinion gear, thereby displacing the platform portion 26 relative to the arm body 28 in smaller increments in the varus-valgus direction 34. Visual markers on either of the platform portion 26 and the arm body 28 can be provided so as to indicate the angular varus-valgus position away from the 0 degree. Alternately, the CAS system may be used to provide this indication.

Figure 17:
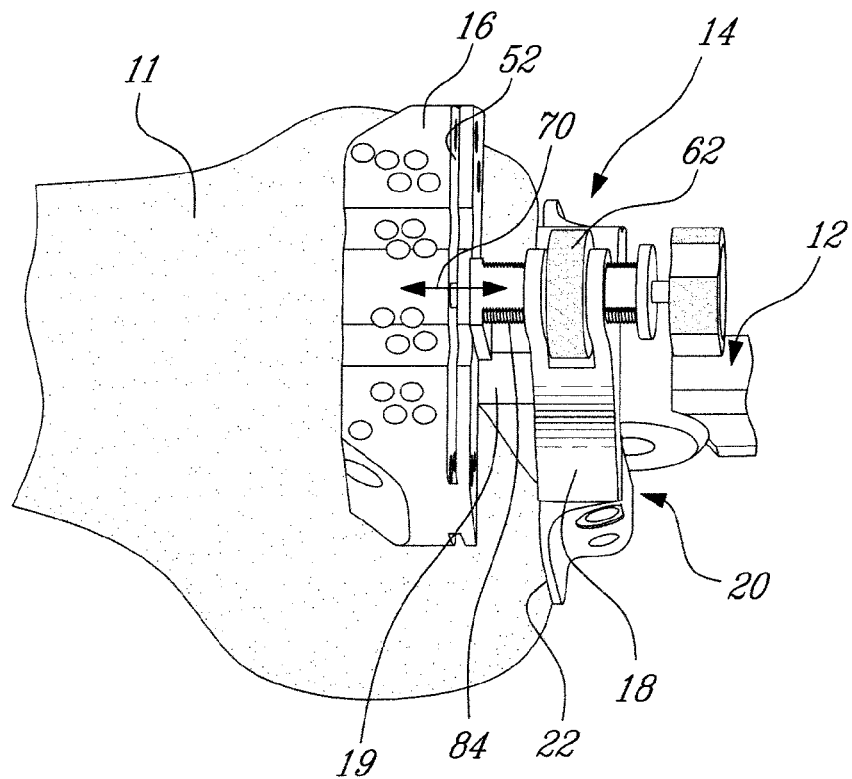
FIG. 17 is top view of the tool guide block assembly and the femur, showing adjustment of the distal resection distance.

Referring now to FIG. 17, the next step performed is to adjust the proximal-distal positioning of the tool guide block 16, and therefore the distance in the proximal direction of the guide block 16 away from the reference surface 22 of the block body 20, which defines a plane in which lies the distal most point on the femur 11. This position of the guide block 16 is selected such as to locate the cutting guide slot 52 defined in the tool guide block 16 at a given position corresponding to the desired distal resection distance. This distal resection distance adjustment is done by rotating the adjustment knob 62 on the platform 18 of the tool guide block assembly 14, thereby translating the tool guide block 16 inward or outward relative to the platform 14 in the proximal-distal direction 70. Indicators 84 are provided on the shaft 64, such as to easily be able to determine the distal resection distance as the tool guide block 16 is displaced proximally in direction 70.

Figure 18:
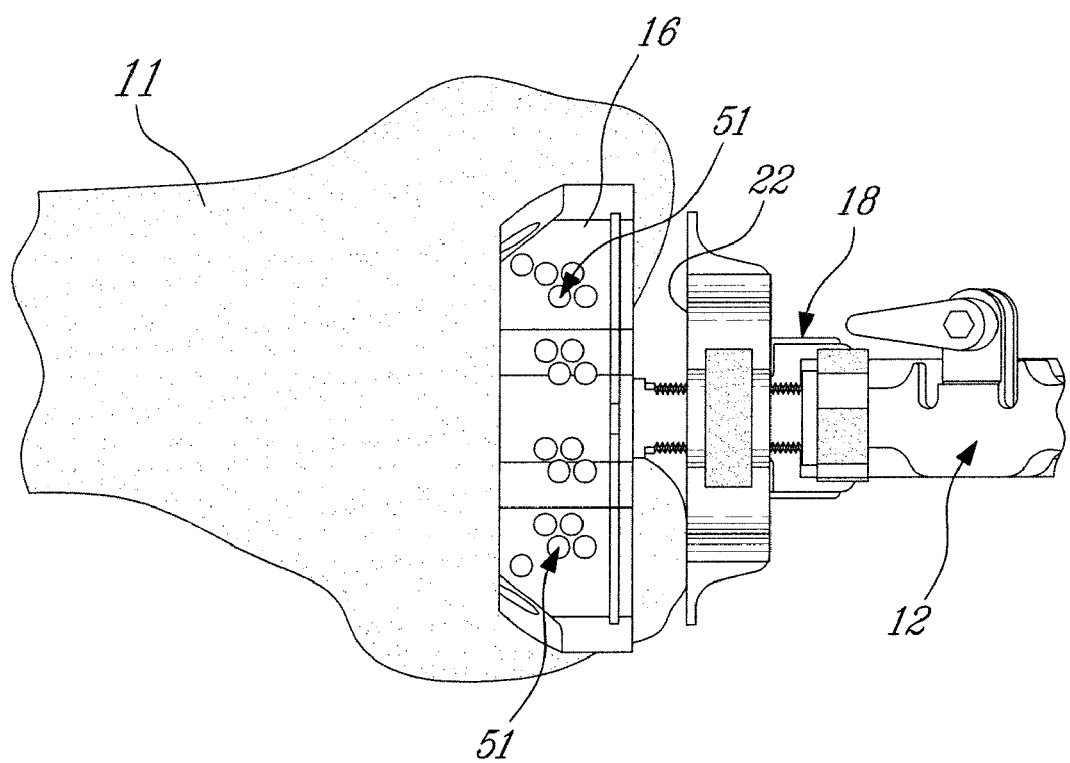
FIG. 18 is top view of the tool guide block assembly and the femur, showing the tool guide block being ready for pinning to the anterior surface of the femoral condyles.
Figure 19:
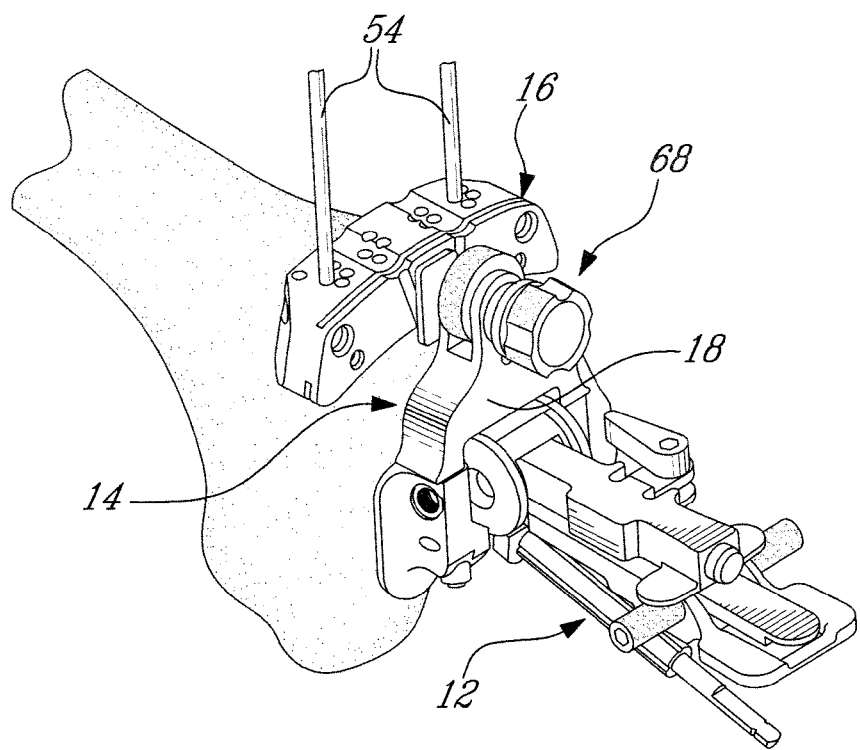
FIG. 19 is a perspective view of the universal positioning device assembly mounted to the femur, showing the disconnection of the positioning device and the platform of the tool guide block assembly being disconnected from the tool guide block which is pinned in place on the femur.

Once the desired distal resection distance has been reached, the tool guide block 16 is pinned in place to the femur 11. First, however, one should make sure that the reference surface 22 of the positioning device 12 remains securely abutted against the distal-most condyle of the femur 11 (i.e. the "reference distal condyle"), as shown in FIG. 18. The tool guide block 16 can then be pinned in place using the first or "0" set of holes 51 defined through the tool guide block 16, best seen in FIG. 18. This may be done by first drilling holes in the bone using these first set of block holes 51 as drill guides, and then inserting the bone pins 54 through these block holes 51 and into the femur 11, such that the tool guide block 16 is securely pinned in place to the anterior surface of the femur 11 as shown in FIG. 19.

Figure 20:
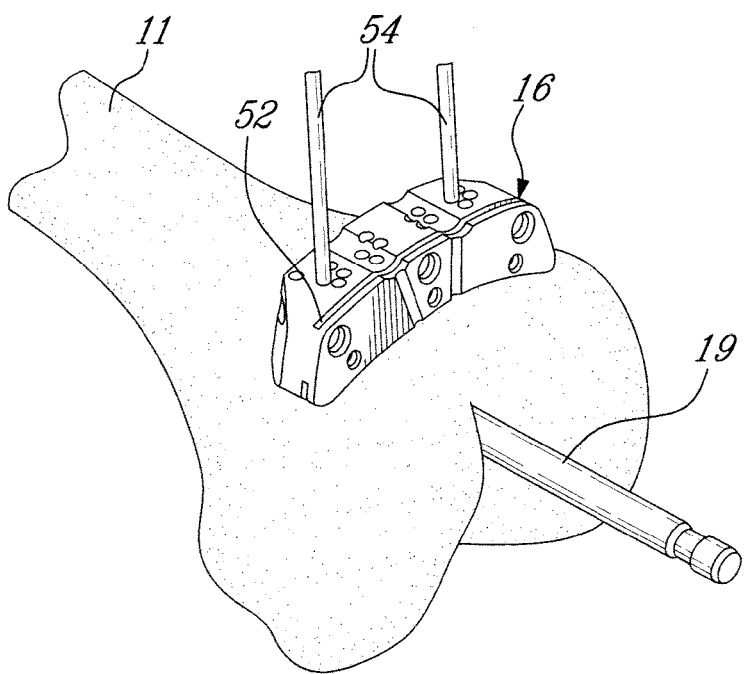
FIG. 20 is a perspective view of the tool guide block which is left pinned in place on the femur.

The rest of the universal positioning device 10 can then be disengaged from the tool guide block 16, which is now securely pinned to the femur 11, by unscrewing the un-coupling knob 68 on the platform 18 of the tool guide 14, in the manner described above. Once the un-coupling knob 68 has been sufficiently turned so that the tool guide block assembly 14 and the positioning device 12 are disconnected from the pinned guide block 16, the entire assembly 10 can then be completely removed by sliding it off the spike 19 in the femur 11. This therefore leaves behind only the tool guide block 16, as shown in FIG. 20, which is now pinned to the femur 11 using pins 54 in a desired position and orientation which permits the distal resection cut to be performed using the saw guide slot 52 in the tool guide block 16 at a predetermined location and angle in femur 11.

Figure 21:
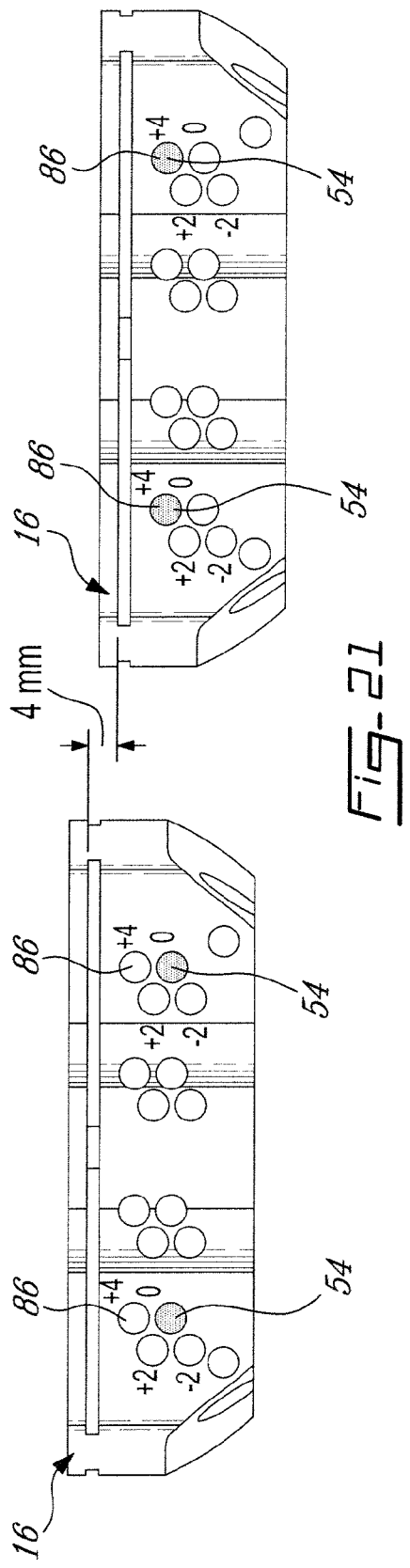
FIG. 21 is a top plan view of two adjacent tool guide blocks showing relative positions of the cutting guide slot relative to pin holes.

FIG. 21 depicts two tool guide blocks 16 adjacent to each other, however this is done for explanation purposed only. Particularly, once the tool guide block 16 is pinned to the femur using the pins 54, which were inserted through the first set of "0" holes 51 in the guide block, it may sometimes become necessary to remove a different amount of bone. Thus, a larger or smaller resection distance than that which was originally calculated or planned for may become necessary. In order to permit this, without having to re-perform the entire procedure described above, additional sets of pin holes are provided in the guide block 16 at specific locations corresponding to measured increments over the initial "0" value. Thus, if it becomes desirable or necessary to resect and additional 4 mm of bone for example, the guide block 16 can simply be slide up and off the pins 54 which remain pinned to the femur, and then re-positioned on the pins 54 but using an alternate set of holes 86, which are labelled on the block as "+4", as shown on the right in FIG. 21. As the holes 86 are defined an exact 4 mm distance from the first set of "0" holes 51, and the pins 54 have remained at the same angle relative to the femur 11, no further repositioning is required to remove an additional 4 mm of bone. A number of such additional sets of holes may be provided in the tool guide block 16, such as to permit −2 mm, +2 mm, +4 mm and +6 mm for example.

Figure 22:
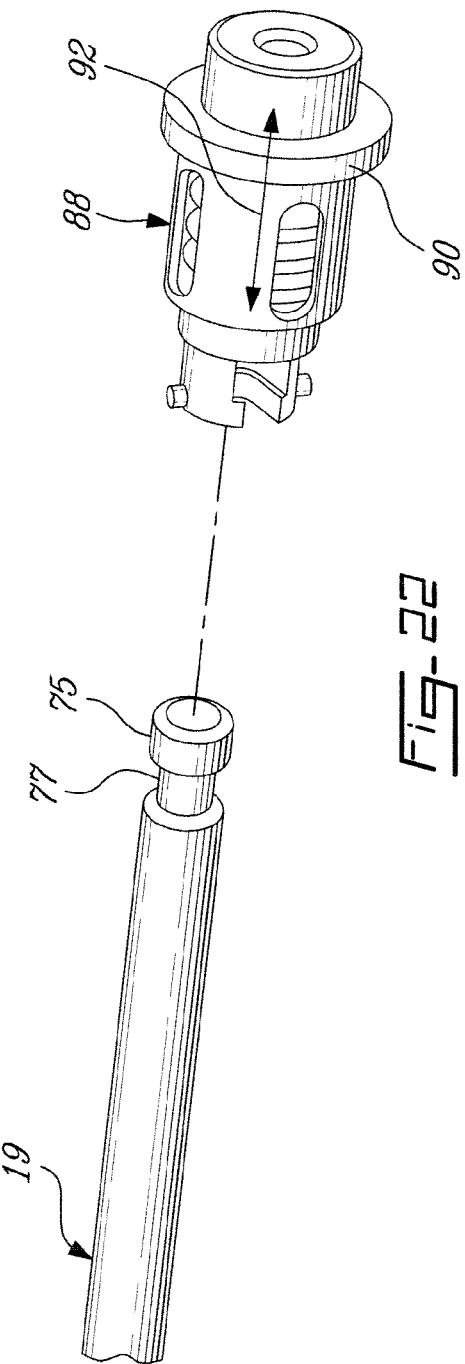
FIG. 22 is a perspective view of the locating spike and associated extraction adapter.

Once the tool guide block 16 is fully pinned in place on the femur, the locating spike 19 can be removed. This may be done in a variety of manners, for example using an extraction adapter 88 as shown in FIG. 22. Particularly, the extraction adapter 88 is placed onto the distal end 75 of the spike 19, and engages the annular channel 77 formed therein. The extraction adapter 88 may be opened for engagement onto the spike 19 by sliding a sleeve 90 thereon in the longitudinal direction 92 indicated. Once on place on the distal end 75 of the spike, the biased sleeve is released, causing the extraction adapter 88 to lock into engagement with the annular channel 77 on the spike's distal end 75. Once so engaged, a standard "slap hammer" may be used to engage the extraction adapter 88 and force the spike 19 out of the femur 19. Other means of extracting the spike 19 from the femur may also be used, either with or without the extraction adapter 88.

Figure 23:
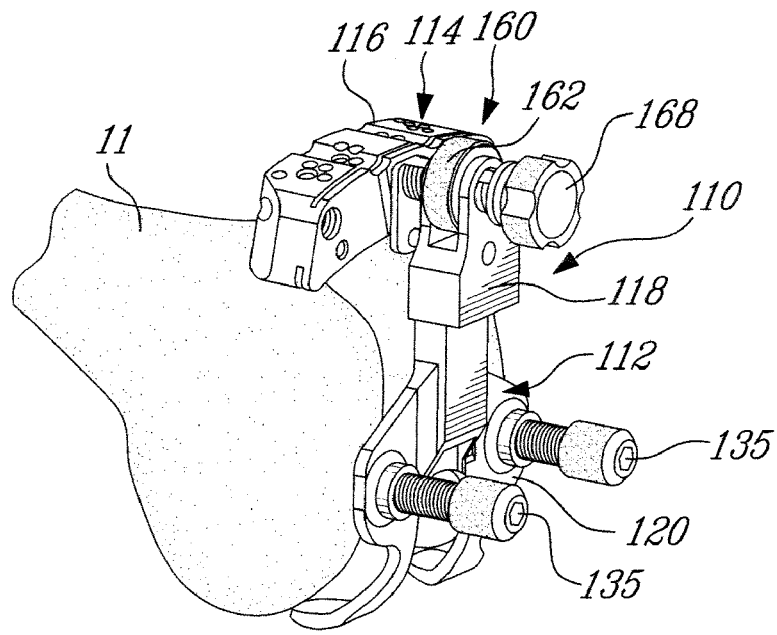
FIG. 23 is a perspective view of a universal positioning device assembly, including a positioning device and a tool guide assembly, in accordance with another embodiment of the present invention.
Figure 24:
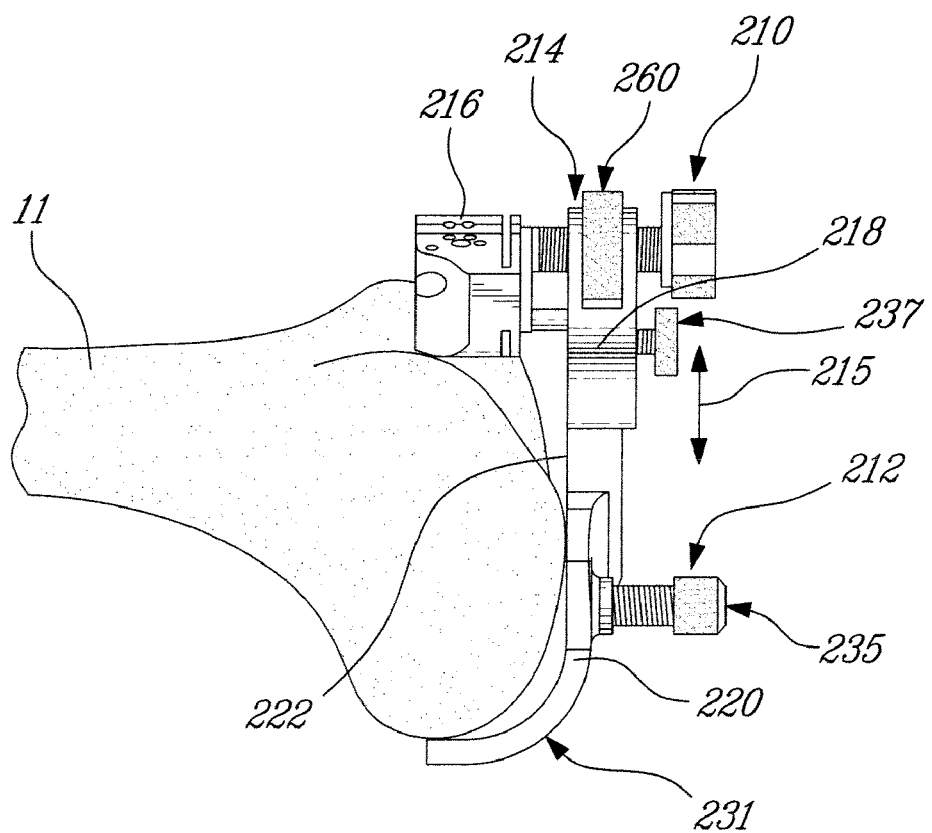
FIG. 24 is a schematic side elevation view of a universal positioning device assembly in accordance with another embodiment of the present invention.
Figure 25:
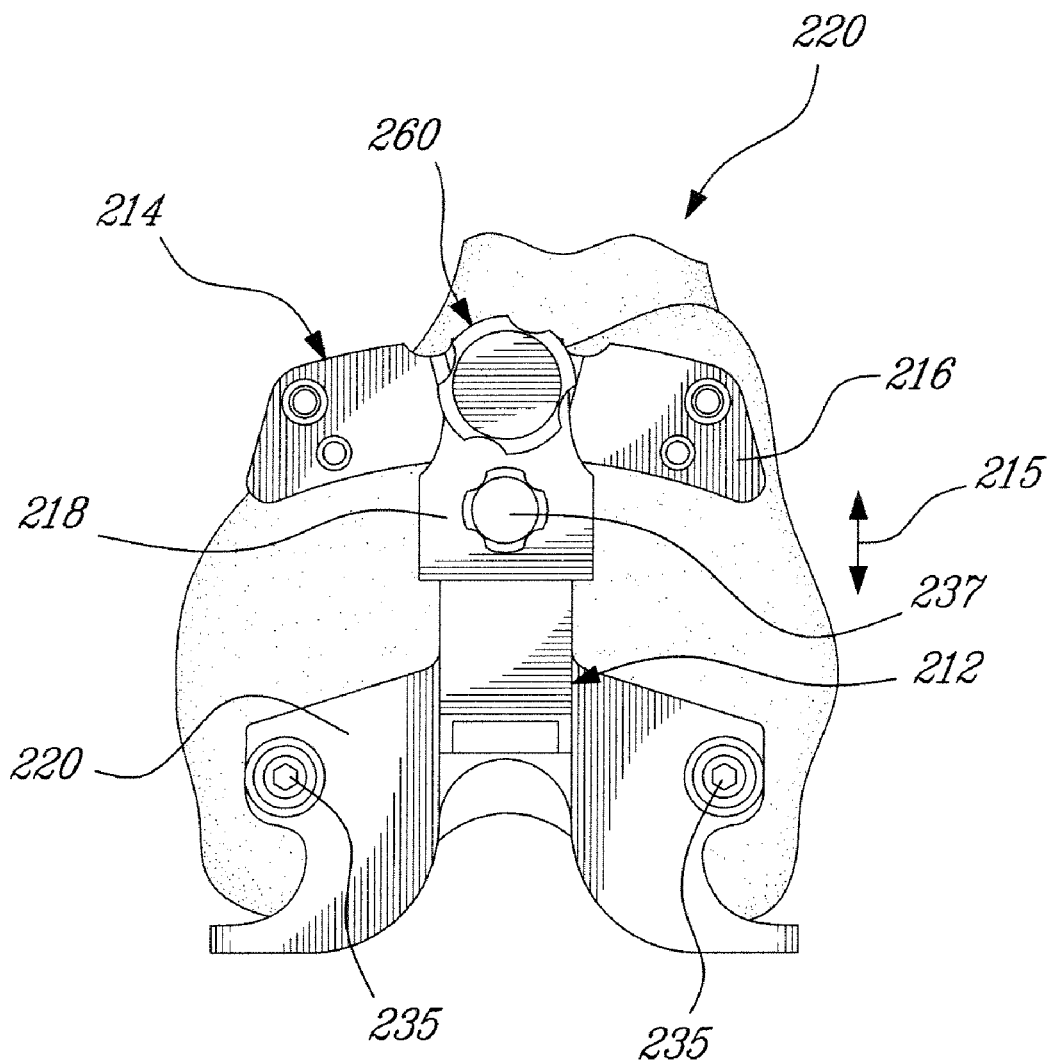
FIG. 25 is an end elevation view of FIG. 24.

Referring now to FIGS. 23-25, a universal positioning device 110 in accordance with an alternate embodiment is depicted. One of the principle differences between this positioning device 110 and the universal positioning device 10 described above is that in this embodiment, the positioning device portion 112 is not fastened to the femur 11 using the spike described above or any other type of bone anchor. As such, the positioning device 110 is intended to be used with an alternate "freehand" guide positioning approach for the femoral preparation in a total knee replacement. While this technique may be slightly less accurate than that described above, wherein the entire guide block assembly is fastened to the femur such as to be able to precisely position the tool guide block, the advantage of this "freehand" option is that it is much less invasive for the patient (in fact it is not invasive at all), given that no bone anchor needs to be fastened to the femur. However, the challenge for such a non-fastened positioning guide is to provide enough stability to keep the tool guide block in a relatively stable position until such time as it is positioned in a desired orientation and pinned in place on the femur.

Accordingly, the universal positioning device 110 includes no bone anchor, and as such is never fastened to the bone while nevertheless still permitting relatively controlled and independent adjustment of the varus-valgus, flexion-extension and distal resection depth values. The universal positioning device assembly 110 includes a positioning device 112, which lacks any sort of mounting point for a spike or intermedular rod, and a tool guide 114 mounted thereto. The tool guide block assembly 114 is as per the tool guide 14 described above, with the exception of the mounting structure of the platform 118 to permit it to be releasably engaged to the positioning device 112. Thus, the tool guide 114 includes the tool guide block 116 mounted to platform 118 via a proximal-distal adjustment mechanism 160 that permits controlled adjustment of the distal resection depth by rotating the adjustment knob 162. Also similarly, the remainder of the entire device 110 can be disconnected from the tool guide block 116 once it is pinned in position by unscrewing the un-coupling knob 168. It is the positioning device 112 which is largely different from that of the universal positioning device 10 described above.

The positioning device 112 includes simply a substantially planar body 120 which includes an inner (or proximally facing) reference surface 122 that is adapted to overly and abut the distal end of the femoral condyles. Medial-lateral adjustment is provided by two spaced apart jack-screws 135, one on the medial side of the body 120 and the other on the lateral side thereof. The proximal ends of these medial-lateral adjustment jack-screws 135 act against the distal end of the femur when rotated, such as to permit adjustment of the varus-valgus positioning angle of the guide block 116. Although the remaining adjustment (i.e. of the flexion-extension angle) direction is not controlled by an adjustment mechanism, relatively controlled variation of this angle can be achieved by carefully "rolling" the entire assembly on the distal end of the femur 11, keeping the inner surface of the planar body 120 in contact with the femur, such as to align the positioning device in a position corresponding to a desired flexion-extension angle. Given that the positioning device 112 is already fairly stable, as it is in mated contact with several points on the condyles of the femur 11, namely the inner surface 122 of the body 120 on positioning device 112 which is abutted against the distal points on the condyles and the tool guide block 116 itself which is abutted on the anterior surfaces of the condyles. These two separate points of contact between the universal positioning device 110 and the femur 11 permit a relatively secure or semi-stable position, despite the positioning device not being fastened to the femur.

These adjustments may be performed using a tracker of an associated CAS system, the tracker being removably mounted to the tool guide block 16/116, such that the CAS system can indicate when the desired position and orientation of the tool guide block 16 is reached. Alternately, the tracker of the CAS system can be mounted to the positioning device portion of the assembly.

Once the tool guide block 116 is located in the desired position and orientation (i.e. the flexion-extension and varus-valgus angles and the distal resection depth have been adjusted and selected as described), the tool guide block 116 can be pinned in place to the anterior side of the femoral condyles, as described in the method above. Preferably, however, when pinning the tool guide block 116 to the femur, the first pin is inserted through the selected hole in the tool guide block 116 on the side of the femur which corresponds to the reference condyle (i.e. that condyle which is the most distal and thus which is used as the reference point throughout). This first pin therefore fixes the flexion-extension angle as well as the distal resection depth, at least on this reference condyle. The tool guide block 116 can then be slightly pivoted about the first pin, such as to permit the fine tuning of the varus-valgus angle if this should be necessary. As the first pin is located on the reference condyle, rotating the tool guide block 116 about this pivot point (i.e. the first pin) does not significantly change the resection thickness measure. Once the desired varus-valgus angle is reached, the second pin can then be installed through the tool guide block 116, thereby fixing it in place for the distal resection cut.

In the embodiment of FIG. 24-25, a universal positioning device assembly 210 in accordance with another embodiment is shown. This assembly is much as per the universal positioning device 110 shown in FIG. 23 and described above, therefore including both a proximal-distal adjustment mechanism 260 on the tool guide 214 to vary the distal resection depth and two jack-screws 235 on the body 220 of the positioning device 212 to vary the varus-valgus angle. However in this embodiment, the body 220 of the positioning device 212 includes posterior forks 131 which extend away from the planar body 22 and are substantially perpendicular thereto. As such, when the inner surface 222 of the planar body 220 is abutted against a distal end of the femur 11, the posterior forks 231 extend proximally and on the posterior side of the femur. Thus, with the posterior forks 231 abutted against the posterior surfaces of the condyles, and additional point of contact between the assembly and the femur is provided, thereby potentially further improving the stability of the assembly during positioning of the tool guide block 216.

However, given that the universal positioning device 210 includes both anterior (i.e. the tool guide block 216) and posterior (i.e. the posterior forks 231) abutment points, adjustment of the device is desirable in this anterior-posterior direction such as to be able to accommodate a variety of different knee sizes. As such, the universal positioning device 210 also includes an anterior-posterior adjustment mechanism 237 which permits the controlled displacement of the body 220 of the positioning device 212 and the platform portion 218 of the tool guide 214 towards and/or away from each other in the anterior-posterior direction 215. Thus, the two abutment portions, namely the posterior forks 231 and the tool guide block 216, can be displaced relative to each other in the anterior-posterior direction 215 such as to be able to accommodate a variety of sizes of femurs 11. Another advantage of this configuration is that rotation of the entire assembly about the femur would then be fixed by the posterior condyles, thus ensuring that by rotating the jack-screws 235 adjusts only the varus-valgus angle and does not impart any flexion component to the displacement of the tool guide block. When used in conjunction with a CAS system, this may also permit the elimination of an otherwise typically employed step of digitizing the posterior condyles, as this can now be done directly with the positioning device 212 of the universal positioning device 210 (given that the posterior forks 231 abut the posterior condyles), provided a CAS tracker is fixed to a portion of the assembly.

The use of the universal positioning device 110/210 has the added advantage of saving time by removing the necessity of installing and then subsequently removing the spike or an intermedular rod, and potentially removing the need to separately digitize the posterior condyles or the distal condyles for a desired resection level, thus simplifying and speeding-up the entire procedure. The other major advantage of the use of either of these assemblies is that they are non-invasive to the patient, given that no bone anchor needs (ex: spike, etc.) to be inserted into the femur.

Although the universal positioning devices 10, 110, 210 have been depicted and described above generally without reference to a CAS tracker which is fastened (temporarily or permanently) thereto, it is to be understood that the devices described herein are able to be used in either a standard surgical procedure (i.e. non-CAS) or used in conjunction with a CAS system. As such, the universal positioning device 10, 110, 210 may be provided with a CAS tracker when used with a CAS system. Such trackers are well known in the art, and typically comprises at least three detectable elements, engaged to the tracker member, which are detected by the CAS system and permit the CAS system to determine the exact position and orientation in three dimensional space of the tracker, and accordingly of the device to which the tracker is fixed. The tracker may be removably mounted to a portion of the universal positioning device 10, 110, 210. For example, the tracker may be mounted to the tool guide block 16, 116, 216, such as by engaging the saw guide slot 52 therein for example. The detectable elements may be, for example, spherical passive markers locatable by a camera-based, optical tracking CAS system. However, it is to be understood that active optical markers may equivalently be used as the detectable elements and that CAS systems using any other type of tracking elements, such as for example electromagnetically and acoustically detectable elements, may also similarly be employed. The tracker member thus permits the CAS system to track the precise position of the expected cutting plane of the surgical tool guide block 16. However, the present 10, 110, 210 can equivalently be used in conventional, or non-computer assisted, surgical applications.

The embodiments of the invention described above are intended to be exemplary. Those skilled in the art will therefore appreciate that the forgoing description is illustrative only, and that various alternatives and modifications can be devised without departing from the spirit of the present invention. Accordingly, the present is intended to embrace all such alternatives, modifications and variances which fall within the scope of the appended claims.

The invention claimed is:

1. A device for positioning a tool guide block, said device comprising:
a positioning device including a block body having an inwardly facing reference surface adapted to abut a bone element, the positioning device including a first adjustment mechanism and a second adjustment mechanism independently operable from the first adjustment mechanism, the first adjustment mechanism permitting rotation of the tool guide block about a medial-lateral extending axis such as to provide flexion-extension angle adjustment, the second adjustment mechanism permitting rotation of the tool guide block about an anterior-posterior extending axis such as to provide varus-valgus angle adjustment, the second adjustment mechanism including a coarse adjustment mechanism and a fine adjustment mechanism;
wherein the positioning device includes a swing arm member pivotally engaged to the block body, the swing arm member having a first portion and a second portion which pivot together relative to the block body about the medial-lateral extending axis; and
a tool guide mounted to the positioning device, the tool guide including a platform portion which is engaged to the block body of the positioning device and the tool guide block which is releasably engaged with the platform.

2. The device as defined in claim 1, wherein the first portion of the swing arm member comprises a lower platform portion and the second portion of the swing arm member comprises a main arm body which rests on top of the lower platform portion, the lower platform portion and the main arm body being connected by a pivoting joint such that they pivot relative to each other about the anterior-posterior extending axis.

3. The device as defined in claim 2, wherein the main arm body includes an opening therethrough for receiving a bone anchor used to fasten the positioning device to the bone element.

4. The device as defined in claim 3, wherein the main arm body remains pivotally fixed relative to the bone anchor and the bone element, and the lower platform portion pivots with said block body.

5. The device as defined in claim 2, wherein the second adjustment mechanism includes a rack and pinion gear mechanism disposed between the lower platform portion and the main arm body.

6. The device as defined in claim 5, wherein the coarse adjustment mechanism includes a cantilevered tab to which one of the rack and the pinion gear is mounted, the tab being displaceable between an engaged position wherein the rack and the pinion gear are connected in meshing engagement, and a disengaged position wherein the rack and the pinion gear are disconnected from each other such that free relative pivotal movement between the lower platform portion and the main arm body about the anterior-posterior extending axis is possible.

7. The device as defined in claim 6, wherein the tab is biased in the engaged position to maintain the rack and the pinion gear in meshing engagement until the tab is depressed by a user thereby displacing the tab into the disengaged position.

8. The device as defined in claim 6, wherein the fine adjustment mechanism includes a screw knob fixed to the pinion gear and operable, when rotated, to displace the rack in a direction substantially parallel to an axis of rotation of the pinion gear in order to provide controlled relative pivotal displacement between the lower platform portion and the main arm body about the anterior-posterior extending axis, thereby permitting an exact value of the varus-valgus angle to be adjusted.

9. The device as defined in claim 1, wherein the first adjustment mechanism includes a pivot joint between the block body and a swing arm member of the positioning device, and a locking adjustment handle mounted to the block body, the adjustment handle being operable to lock the arm member in a fixed pivotal position about the medial-lateral extending axis relative to the block body, thereby fixing the flexion-extension angle at a desired value.

10. The device as defined in claim 1, wherein the tool guide block is displaceable by a proximal-distal adjustment mechanism relative to the reference surface of the block body in a direction substantially parallel to a proximal-distal axis relative to the bone element.

11. The device as defined in claim 1, further comprising a bone anchor to which the positioning device is releasably fasteneable.

12. The device as defined in claim 11, wherein the positioning device is releasably fastenable to the bone anchor such that at least a portion of the positioning device is restricted in movement in all directions but for along a proximal-distal axis relative to the bone element.

13. The device as defined in claim 11, wherein the positioning device is fixed in place on the bone anchor by a locking mechanism having a locking lever which is displaceable between a locked position, wherein a friction clamp engages the bone anchor, and an unlocked position, wherein the positioning device is free to slide along a length of the bone anchor.

14. The device as defined in claim 11, wherein the bone anchor includes a spike defining a longitudinal axis and having a radially protruding pin thereon, the pin being received within a correspondingly shaped channel in the positioning device, such that when the pin and the channel are aligned and interlocked, the positioning device is prevented from rotating around the longitudinal axis of the spike.

15. The device as defined in claim 11, wherein the bone anchor defines a longitudinal axis and has a non-circular cross-sectional shape, the bone anchor being is received within a correspondingly shaped channel in the positioning device thereby preventing rotation of the positioning device around the longitudinal axis of the bone anchor.

16. The device as defined in claim 1, wherein the positioning device is a universal positioning device for use in orthopedic knee replacement surgery.

17. The device as defined in claim 1, further comprising a computer assisted surgery (CAS) system in communication with the device, the CAS system being operable to determine at least the orientation and movement of the positioning device or tool guide in three dimensional space.

18. A device for use in orthopedic knee replacement surgery on a femur, said device comprising:
a positioning device including a block body having an inwardly facing reference surface adapted to abut a distal end of the femur, the positioning device including a first adjustment mechanism and a second adjustment mechanism independently operable from the first adjustment mechanism;
wherein the positioning device includes a swing arm member pivotally engaged to the block body, the swing arm member having a first portion and a second portion which pivot together relative to the block body about the medial-lateral extending axis;
a tool guide mounted to the positioning device, the tool guide including a platform portion which is engaged to the block body of the positioning device and a tool guide block which is releasably engaged with the platform; and
wherein the first adjustment mechanism permits rotation of the tool guide block about a medial-lateral extending axis such as to provide flexion-extension angle adjustment, the second adjustment mechanism permitting rotation of the tool guide block about an anterior-posterior extending axis such as to provide varus-valgus angle adjustment, the second adjustment mechanism including a coarse adjustment mechanism and a fine adjustment mechanism.

19. A device for use in orthopedic knee replacement surgery on a femur, said device comprising:
a positioning device including a block body having a first inwardly facing reference surface adapted to abut a distal end of the femur and a second reference surface adapted to abut a posterior side of the femur, the second reference surface being substantially perpendicular to the first reference surface, the positioning device being positionable relative to the femur without being fastened thereto;
wherein the positioning device includes a swing arm member pivotally engaged to the block body, the swing arm member having a first portion and a second portion which pivot together relative to the block body about the medial-lateral extending axis;
a tool guide mounted to the positioning device, the tool guide including a platform portion which is engaged to the block body of the positioning device and a tool guide block which is releasably engaged with the platform via a proximal-distal adjustment mechanism permitting the tool guide block to be displaced relative to the platform, and thus the first inwardly facing reference surface of the positioning device, in a direction substantially perpendicular to the first reference surface, such as to adjust a distal resection depth in the femur; and
a varus-valgus adjustment mechanism independently operable from the proximal-distal adjustment mechanism and provided in the block body of the positioning device for adjustment of a varus-valgus angle of the block body relative to the femur and therefore the varus-valgus angle of the tool guide block mounted to the positioning device.

20. The device as defined in claim 19, wherein the varus-valgus adjustment mechanism includes two jack-screws spaced apart in a medial-lateral direction and being independently actuable to act directly on the distal end of the femur.

21. The device as defined in claim 19, wherein the block body of the positioning device includes posterior forks which extend away from the first reference surface and are substantially perpendicular thereto.

22. The device as defined in claim 19, further comprising a computer assisted surgery (CAS) system in communication with the device, the CAS system being operable to determine one or more of the position, orientation and movement of the positioning device or tool guide assembly in three dimensional space.

23. The device as defined in claim 22, wherein the CAS system is in communication with the tool guide block for determining at least the orientation of the tool guide block.

* * * * *